United States Patent
Shimp et al.

(10) Patent No.: US 8,642,061 B2
(45) Date of Patent: Feb. 4, 2014

(54) METHOD OF TREATING BONE TISSUE

(75) Inventors: Lawrence A. Shimp, Morganville, NJ (US); Guobao Wei, Eatontown, NJ (US); Keyvan Behnam, Simi Valley, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1213 days.

(21) Appl. No.: 12/140,062

(22) Filed: Jun. 16, 2008
(Under 37 CFR 1.47)

(65) Prior Publication Data
US 2009/0087471 A1 Apr. 2, 2009

Related U.S. Application Data

(60) Provisional application No. 60/944,408, filed on Jun. 15, 2007.

(51) Int. Cl.
*A61K 35/32* (2006.01)

(52) U.S. Cl.
USPC .............................. 424/422; 424/549; 422/33

(58) Field of Classification Search
None
See application file for complete search history.

(56) References Cited

U.S. PATENT DOCUMENTS

| | | | |
|---|---|---|---|
| 2,369,139 A * | 2/1945 | Deitz | 502/426 |
| 2,742,488 A * | 4/1956 | Dufault | 554/22 |
| 3,476,855 A * | 11/1969 | Balassa | 424/548 |
| 4,172,128 A | 10/1979 | Thiele et al. | |
| 4,294,753 A | 10/1981 | Urist | |
| 4,394,370 A | 7/1983 | Jefferies | |
| 4,430,760 A | 2/1984 | Smestad | |
| 4,440,370 A | 4/1984 | Rood | |
| 4,440,750 A | 4/1984 | Glowacki et al. | |
| 4,455,256 A | 6/1984 | Urist | |
| 4,472,840 A | 9/1984 | Jefferies | |
| 4,485,097 A | 11/1984 | Bell | |
| 4,563,350 A | 1/1986 | Nathan et al. | |
| 4,619,989 A | 10/1986 | Urist | |
| 4,657,548 A | 4/1987 | Nichols | |
| 4,678,470 A | 7/1987 | Nashef et al. | |
| 4,743,259 A | 5/1988 | Bolander et al. | |
| 4,755,184 A | 7/1988 | Silverberg | |
| 4,761,471 A | 8/1988 | Urist | |
| 4,774,228 A | 9/1988 | Seyedin et al. | |
| 4,774,322 A | 9/1988 | Seyedin et al. | |
| 4,787,906 A | 11/1988 | Haris | |
| 4,789,663 A | 12/1988 | Wallace et al. | |
| 4,789,732 A | 12/1988 | Urist | |
| 4,795,804 A | 1/1989 | Urist | |
| 4,804,744 A | 2/1989 | Sen | |
| 4,810,691 A | 3/1989 | Seyedin et al. | |
| 4,843,063 A | 6/1989 | Seyedin et al. | |
| 4,902,296 A | 2/1990 | Bolander et al. | |
| 5,041,138 A | 8/1991 | Vacanti et al. | |
| 5,073,373 A | 12/1991 | O'Leary | |
| 5,106,748 A | 4/1992 | Wozney et al. | |
| 5,166,187 A | 11/1992 | Collombel et al. | |
| 5,211,664 A | 5/1993 | Tepic et al. | |
| 5,236,456 A | 8/1993 | O'Leary et al. | |
| 5,266,683 A | 11/1993 | Oppermann et al. | |
| 5,270,300 A | 12/1993 | Hunziker | |
| 5,284,655 A | 2/1994 | Bogdansky et al. | |
| 5,290,558 A | 3/1994 | O'Leary et al. | |
| 5,290,763 A | 3/1994 | Poser et al. | |
| 5,314,476 A | 5/1994 | Prewett et al. | |
| 5,336,264 A | 8/1994 | Constanz et al. | |
| 5,354,557 A | 10/1994 | Oppermann et al. | |
| 5,378,469 A | 1/1995 | Kemp et al. | |
| 5,385,887 A | 1/1995 | Yim et al. | |
| 5,405,390 A | 4/1995 | O'Leary et al. | |
| 5,490,962 A | 2/1996 | Cima et al. | |
| 5,501,706 A | 3/1996 | Arenberg | |
| 5,507,813 A | 4/1996 | Dowd et al. | |
| 5,518,680 A | 5/1996 | Cima et al. | |
| 5,531,735 A | 7/1996 | Thompson | |
| 5,563,124 A | 10/1996 | Damien et al. | |
| 5,571,189 A | 11/1996 | Kuslich | |
| 5,607,269 A | 3/1997 | Dowd et al. | |
| 5,618,339 A | 4/1997 | Ito | |

(Continued)

FOREIGN PATENT DOCUMENTS

DE 2 253 086 9/1974
DE 693 24 117 T2 6/1994

(Continued)

OTHER PUBLICATIONS

Zhou et al, Acta Orthop Belg, Oct. 2011, vol. 77, No. 5, pp. 670-675 (abstract only).*

(Continued)

*Primary Examiner* — Allison Ford
(74) *Attorney, Agent, or Firm* — Sorell Lenna & Schmidt LLP

(57) ABSTRACT

In one embodiment, the method comprises providing tissue, preparing the tissue, and treating the tissue to improve remodeling characteristics of the tissue. The tissue may be, for example, cortical bone. Treating the tissue to improve remodeling characteristics may comprise heating the tissue, treating the tissue with a chemical, or other. Heating the tissue may be done in the absence of oxygen and may comprise heating the tissue in a vacuum, heating the tissue in an inert atmosphere, heating the tissue in a reducing atmosphere, coating the tissue with a protective coating and heating the tissue, or other. Further embodiments comprise treating the tissue in supercritical fluids, for example, to dry or virally inactivate the tissue.

20 Claims, 7 Drawing Sheets

(56) References Cited

U.S. PATENT DOCUMENTS

| | | |
|---|---|---|
| 5,658,882 A | 8/1997 | Celeste et al. |
| 5,723,012 A | 3/1998 | Fages et al. |
| 5,725,579 A | 3/1998 | Fages et al. |
| 5,776,193 A | 7/1998 | Kwan et al. |
| 5,788,959 A | 8/1998 | Singh |
| 5,807,437 A | 9/1998 | Sachs et al. |
| 5,830,493 A | 11/1998 | Yokota et al. |
| 5,846,484 A | 12/1998 | Scarborough et al. |
| 5,877,005 A | 3/1999 | Castor et al. |
| 5,894,070 A | 4/1999 | Hansson et al. |
| 5,899,939 A | 5/1999 | Boyce et al. |
| 5,902,562 A | 5/1999 | Lagasse et al. |
| 5,912,131 A | 6/1999 | Eyre |
| 6,007,580 A | 12/1999 | Lehto et al. |
| 6,018,095 A | 1/2000 | Lerch et al. |
| 6,030,635 A | 2/2000 | Gertzman et al. |
| 6,117,646 A | 9/2000 | Qvist et al. |
| 6,120,558 A | 9/2000 | Poddevin et al. |
| 6,124,273 A | 9/2000 | Drohan et al. |
| 6,143,030 A | 11/2000 | Schroder |
| 6,149,864 A | 11/2000 | Dillow et al. |
| 6,162,258 A | 12/2000 | Scarborough et al. |
| 6,180,606 B1 | 1/2001 | Chen et al. |
| 6,197,325 B1 | 3/2001 | MacPhee et al. |
| 6,217,614 B1 | 4/2001 | Fages et al. |
| 6,245,537 B1 | 6/2001 | Williams et al. |
| 6,294,041 B1 | 9/2001 | Boyce et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,352,667 B1 | 3/2002 | English |
| 6,372,257 B1 | 4/2002 | Marchosky |
| 6,387,391 B1 | 5/2002 | Shikinami et al. |
| 6,436,138 B1 | 8/2002 | Dowd et al. |
| 6,440,444 B2 | 8/2002 | Boyce et al. |
| 6,465,168 B1 | 10/2002 | Castor et al. |
| 6,468,543 B1 | 10/2002 | Gilbertson et al. |
| 6,478,825 B1 | 11/2002 | Winterbottom et al. |
| 6,592,886 B1 | 7/2003 | Zimmermann |
| 6,595,998 B2 | 7/2003 | Johnson et al. |
| 6,599,515 B1 | 7/2003 | Delmotte |
| 6,616,698 B2 | 9/2003 | Scarborough |
| 6,618,698 B1 | 9/2003 | Beausoleil et al. |
| 6,623,749 B2 | 9/2003 | Williams et al. |
| 6,648,919 B2 | 11/2003 | Ferree |
| 6,696,073 B2 | 2/2004 | Boyce et al. |
| RE38,522 E | 5/2004 | Gertzman et al. |
| 6,740,093 B2 | 5/2004 | Hochschuler et al. |
| 6,752,831 B2 | 6/2004 | Sybert et al. |
| 6,783,546 B2 | 8/2004 | Zucherman |
| 6,843,807 B1 | 1/2005 | Boyce et al. |
| 6,884,428 B2 | 4/2005 | Binette et al. |
| 6,884,778 B2 | 4/2005 | Jo et al. |
| 6,911,212 B2 | 6/2005 | Gertzman et al. |
| 6,953,594 B2 | 10/2005 | Lee et al. |
| 6,969,404 B2 | 11/2005 | Ferree |
| 6,989,029 B2 | 1/2006 | Bonutti |
| 7,001,390 B2 | 2/2006 | Gebhardt et al. |
| 7,008,591 B2 | 3/2006 | Kafesjian et al. |
| 7,019,192 B2 | 3/2006 | Gertzman et al. |
| 7,025,771 B2 | 4/2006 | Kuslich et al. |
| 7,045,141 B2 | 5/2006 | Merboth et al. |
| 7,060,287 B1 | 6/2006 | Hubbard et al. |
| 7,108,832 B2 | 9/2006 | Christensen et al. |
| 7,163,691 B2 | 1/2007 | Knaack et al. |
| 7,179,299 B2 | 2/2007 | Edwards et al. |
| 7,208,015 B2 | 4/2007 | Pointillart et al. |
| 7,220,282 B2 | 5/2007 | Kuslich |
| 7,226,481 B2 | 6/2007 | Kuslich |
| 7,241,303 B2 | 7/2007 | Reiss et al. |
| 7,261,720 B2 | 8/2007 | Stevens et al. |
| 8,007,718 B1 * | 8/2011 | Biberger .......... 422/28 |
| 2001/0031254 A1 | 10/2001 | Bianchi et al. |
| 2001/0043258 A1 | 11/2001 | Ohki |
| 2002/0058947 A1 | 5/2002 | Hochschuler et al. |
| 2002/0068974 A1 | 6/2002 | Kuslich et al. |
| 2002/0077701 A1 | 6/2002 | Kuslich |
| 2002/0133166 A1 | 9/2002 | McKay et al. |
| 2002/0197297 A1 | 12/2002 | Risbud et al. |
| 2003/0008328 A1 | 1/2003 | Wironen et al. |
| 2003/0039676 A1 | 2/2003 | Boyce et al. |
| 2003/0044445 A1 | 3/2003 | Kay et al. |
| 2003/0065392 A1 | 4/2003 | Fan et al. |
| 2003/0072677 A1 | 4/2003 | Kafesjian et al. |
| 2003/0129178 A1 | 7/2003 | Wegman et al. |
| 2003/0143258 A1 | 7/2003 | Knaack et al. |
| 2003/0152548 A1 | 8/2003 | Mikos et al. |
| 2003/0194708 A1 | 10/2003 | Binnerts et al. |
| 2004/0023387 A1 | 2/2004 | Morris et al. |
| 2004/0024457 A1 | 2/2004 | Boyce et al. |
| 2004/0059364 A1 | 3/2004 | Gaskins et al. |
| 2004/0072322 A1 | 4/2004 | Thorne |
| 2004/0146543 A1 | 7/2004 | Shimp et al. |
| 2004/0220615 A1 | 11/2004 | Lin |
| 2004/0249464 A1 | 12/2004 | Bindseil et al. |
| 2005/0008620 A1 | 1/2005 | Shimp et al. |
| 2005/0008672 A1 | 1/2005 | Winterbottom et al. |
| 2005/0020506 A1 | 1/2005 | Drapeau et al. |
| 2005/0027033 A1 | 2/2005 | Knaack et al. |
| 2005/0037978 A1 | 2/2005 | Damien |
| 2005/0131417 A1 | 6/2005 | Ahern et al. |
| 2005/0244450 A1 | 11/2005 | Reddi |
| 2005/0244457 A1 | 11/2005 | Reddi |
| 2005/0251267 A1 | 11/2005 | Winterbottom et al. |
| 2005/0283255 A1 | 12/2005 | Geremakis et al. |
| 2006/0216321 A1 | 9/2006 | Lyu et al. |
| 2006/0216323 A1 | 9/2006 | Knaack et al. |
| 2006/0287732 A1 | 12/2006 | Pezeshkian |
| 2007/0073401 A1 | 3/2007 | Pointillart et al. |
| 2007/0093896 A1 | 4/2007 | Malinin |
| 2007/0098756 A1 | 5/2007 | Behnam |
| 2007/0110820 A1 | 5/2007 | Behnam |
| 2007/0118222 A1 | 5/2007 | Lang |
| 2007/0125700 A1 | 6/2007 | Ding et al. |
| 2007/0142916 A1 | 6/2007 | Olson et al. |
| 2007/0154563 A1 | 7/2007 | Behnam et al. |
| 2007/0162132 A1 | 7/2007 | Messerli |
| 2007/0178158 A1 | 8/2007 | Knaack et al. |
| 2007/0231788 A1 | 10/2007 | Behnam et al. |
| 2008/0027546 A1 | 1/2008 | Semler et al. |
| 2008/0069852 A1 | 3/2008 | Shimp et al. |
| 2008/0091270 A1 | 4/2008 | Miller et al. |
| 2008/0260794 A1 | 10/2008 | Lauritzen et al. |
| 2009/0130173 A1 | 5/2009 | Behnam et al. |
| 2009/0155378 A1 | 6/2009 | Behnam et al. |
| 2009/0157087 A1 | 6/2009 | Wei et al. |
| 2009/0192474 A1 | 7/2009 | Wei et al. |
| 2009/0220605 A1 | 9/2009 | Wei et al. |

FOREIGN PATENT DOCUMENTS

| | | |
|---|---|---|
| EP | 0 082 621 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 0 603 920 A1 | 6/1994 |
| EP | 0 621 020 A1 | 10/1994 |
| EP | 0781564 A2 | 7/1997 |
| JP | 01/179689 | 7/1989 |
| WO | WO 88/00205 | 1/1988 |
| WO | WO 88/01517 | 3/1988 |
| WO | WO 90/03733 | 4/1990 |
| WO | WO 94/21298 | 9/1994 |
| WO | WO 95/31948 | 11/1995 |
| WO | WO 96/39170 | 12/1996 |
| WO | WO 00/13615 | 3/2000 |
| WO | WO 00/45870 | 8/2000 |
| WO | WO 00/47736 | 8/2000 |
| WO | WO 01/28461 A2 | 4/2001 |
| WO | WO 01/70136 A2 | 9/2001 |
| WO | WO 01/79342 A2 | 10/2001 |

(56) References Cited

FOREIGN PATENT DOCUMENTS

| | | |
|---|---|---|
| WO | WO 02/069818 A2 | 9/2002 |
| WO | WO 03/025271 A1 | 3/2003 |
| WO | WO 03/030956 A3 | 4/2003 |
| WO | WO 2004/073563 A | 9/2004 |
| WO | WO 2005/065396 A2 | 7/2005 |
| WO | WO 2005/072656 A1 | 8/2005 |
| WO | WO 2005/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Landesman, Richard et al., "In Vivo Analysis of the Half-Life of the Osteoinductive Potential of Demineralized Bone Matrix Using Diffusion Chambers", *Calcif. Tissue Int.*, vol. 45, No. 6 1989, 348-353.

Laursen, Malene et al., "Optimal Handling of fresh cancellous bone graft-Different peroperative storing techniques evaluated by in vitro osteobalst-like cell metabolism", *Acta Orthop Scand.*, vol. 74, No. 4 2003, 491.

Ou, Wenbin et al. "Effects of Glycerol in the Refolding and Unfolding of Creatine Kinase," *Tsinghua Science and Technology*, 7(4): 352-367 (Aug. 2002).

Ou, Wenbin et al. "Molecular Mechanism for Osmolyte Protection of Creatine Kinase Against Guanidine Denaturation," *Eur. J. Biochem.*, 268: 5901-5911 (2001).

Glowacki et al., "Fate of Mineralized and Demineralized Osseous Implants in Crania Defects", *Calcified Tissue International*, vol. 33, pp. 8pgs (1981).

Neigel, et al., "Use of Demineralized Bone Implants in Orbital and Craniofacial Reconstruction and a Review of the Literature", *Ophthalmic Plastic and Reconstructive Surgery*, vol. 12, No. 2, pp. 108-120 (1996).

Urist, M., "Bone: Formation by Autoinduction", *Science*, vol. 150, No. 3698, 9pgs. (Nov. 1965).

Urist, et. al., "Bone Induction Principle", *Clinical Orthopaedics and Related Research*, No. 53, pp. 243-283 (Jul.-Aug. 1967).

White, et al., "Effective terminal sterilization using supercritical carbon dioxide", *Journal of Biotechnology*, 123, pp. 504-515 (2006).

Whiteman, et al., "Demineralized Bone Powder", *The Journal of Hand Surgery*, British and European vol. 18B, No. 4, pp. 487-490 (Aug. 1993).

Xiaobo, et al., "Experimental and Clinical Investigations of Human Insoluble Bone Matrix Gelatin", *Clinical Orthopaedics and Related Research*, No. 293, pp. 360-365 (1993).

Aspenberg et al., "Monkey Bone Matrix Induces Bone Formation in the Athymic Rat, but Not in Adult Monkeys," *J. of Orthop. Res.* 9:20-25 (1991).

Aspenberg P. et al., "Bone morphogenetic protein induces bone in the squirrel monkey, but bone matrix does not", *Acta Orthop Scand.* 63(6): 619-22 (Dec. 1992).

Blumenthal et al. "The use of collagen membrane barriers in conjunction with combined demineralized bone-collagen gel implants in human infrabony defects," *J. Periodontal* 61(6): 319-327 (Jun. 1990).

Bolander et al.,"The Use of Demineralized Bone Matrix in the Repair of Segmental Defects", *The Journal of Bone and Joint Surgery*, 68-A (8): 1264-1273, 1986.

Bravo, D.A. et al., "Accurate and Efficient Cleavage of the Human Insulin Proreceptor by the Human Proprotein-Processing Protease Furin," *Journal Biol Chem.* 269: 25830-25873.

Cameron, A. et al., "Polyarginines are potent inhibitors," *J. Biol. Chem.* 275: 36741-36749 (2000).

Canalis et al., "Bone morphogenetic proteins, their antagonists, and the skeleton," *Endocrine Rev.* 24(2): 218-235 (2003).

Canalis et al., "Stimulation of DNA and Collagen Synthesis by Autologous Growth Factor in Cultured Fetal Rat Calvaria," *Science*, 210:1021-1023 (1980).

Caplanis et al., "Effect of allogenic freeze-dried demineralized bone matrix on guided tissue regeneration in dogs," *J. Periodontal*, 851-856 (Aug. 1998).

Constantino, et al. "Bone Healing and Bone Substitutes," *Facial Plastic Surgery* 18(1): pp. 14-26 (2002).

Crowe et al., "Inhibition of Enzymatic Digestion of Amylose by Free Fatty Acids in Vitro Contributes to Resistant Starch Formation", *J. Nutr.*, 130(8): 2006-2008 (2000).

Cui et al., "The activity and signaling range of mature BMP-4 is regulated by sequential cleavage at two sites within the prodomain of the precursor," *Genes and Development*, 15:2797-2802 (2001).

Cui et al., "BMP-4 is proteolytically activated by furin and/or PC6 during vertebrae embryonic development," *The Embo Journal*, 17(16):4735-4743 (1998).

Deatherage et al., "Packaging and Delivery of Bone Induction Factors in a Collagenous Implant," *Collagen Rel. Res.* 7:225-231 (1987).

Driessens et al., "Calcium Phosphate Bone Cements," Universitat Politecnica de Catalunya, Barcelona, Spain, 31: 855-77.

Dubois et al., "Evidence that Furin Is an Authentic Transforming Growth Facto-B-1-Converting Enxyme," *American Journal of Pathology*, 158(1):305-316 (2001).

Edwards et al., "Osteoinduction of Human Demineralized Bone: Characterization in a Rat Model," *Clinical Orthopaedics & Rel. Res.*, 357: 219-228 (Dec. 1998).

Elliott, J.C., "Structure and Chemistry of the Apatites and Other Calcium Orthophosphates", Elsevier Science B.V., Amsterdam (1994).

Enlow, Donald H., "Principles of Bone Remodeling: An Account of Post-natal Growth and remodeling Processes in Long Bones and the Mandible," Charles C. Thomas, Springfield, Ill., (1963).

Farley et al., "Human Skeletal Growth Factor: Characterization of the Mitogenic Effect on Bone Cells in Vitro," *Biochem*, 21:3508-3513 (1982).

Flemmig, et al. "Long-Term Maintenance of Alveolar Bone Gain After Implantation of Autolyzed, Antigen-Extracted, Allogenic Bone in Periodontal Intraosseous Defects," *J. Periodontal*, 69(1): 47-53 (Jan. 1998).

Fujishiro, et al. "Histological evaluation of an impacted bone graft substitute composed of a combination of mineralized and demineralized allograft in a sheep vertebral bone defect," *Journal of Biomedical Materials Research Part A*, 538-544 (Aug. 4, 2006).

Gamradt, et al. "Bone Graft for Revision Hip Arthroplasty", *Clin. Ortho. and Related Research*, 417: 183-194 (2003).

Gepstein et al. "Bridging Large Defects in Bone by Demineralized Bone Matrix in the Form of a Powder," *The Journal of Bone and Joint Surgery*, 69A(7): 984-991 (1987).

Glowacki, "Cellular Reactions to Bone-Derived Material," *Clin. Ortho. and Related Research*, 324: 47-54 (1996).

Glowacki et al., "Demineralized bone implants," *Symposium on Horizons in Plastic Surgery*, 12(2): 233-41 (1985).

Han B., et al., "Quantitive and sensitive in vitro assay for osteoinductive activity of demineralized bone matrix," *J. Orthop. Res.* 21(4): 648-54 (Jul. 2003).

Han, C. et al. "Autolysed Antigen-Extracted Allogeneic Boen for Repair of Diaphyseal Boen Defects in Rabbits," *Yonsei Medical Journal*, 31(3): 251-257 (1990).

Hollinger, et al. "A comparison of four particulate bone derivatives," *Clin. Ortho. and Related Research*, 267: 255-263 (Jun. 1991).

Hunziker et al., "Repair of Partial Thickness Defects in Articulate Cartilage: Cell Recruitment From the Synovial Membrane", *Journal Bone Joint Surg.*, 78-A: 721-733 (1996).

Iwata et al. "Chemosterilized Autolyzed Antigen-Extracted Allogeneic (AAA) Bone Matrix Gelatin for Repair of Defects from Excision of Benign Bone Tumors," *Clin. Ortho and Related Research*, 154: 150-155 (1981).

Jain et al., "Anchoring of phospholipase $A_2$: the effect of anions and deuterated water, and the role of N-terminus region," *Biochem. Et Biophys. Acta*, 860: 448-461 (1986).

Janovec, et al. "Autolyzed Antigen-Extracted Allogeneic Bone for Bridging Segmented Diaphyseal Bone Defects in Rabbits," *Clin. Ortho. and Related Research*, 229: 249-256 (Apr. 1988).

Jean et al., "Alpha 1-Antitrypsin Portland, a bioengineered serpin highly selective for furin: Application as an antipathogenic agent", *Proc. Natl. Acad. Sci.*, USA 95: 7293-7298 (1998).

(56) References Cited

OTHER PUBLICATIONS

Johnson et al. "Human Bone Mortphogenetic Protein Allografting for Reconstruction of Femoral Nonunion," *Clin. Ortho. and Related Research*, 371: 61-74 (2000).

Johnson et al. "Preliminary explorations of reconstructive surgery with implants of autolyzed antigen-extracted allogeneic (AAA) bone supercharged with bone morphogenetic protein (BMP)," *Bone Grafts, Derivatives and Substitutes*, published by Butterworth-Heinemann, Oxford, pp. 363-376 (1994).

Johnson et al. "Resistant Nonunions and Partial or Complete Segmental Defects of Long Bones," *Clin. Ortho. and Related Research*, 277: 229-237 (Apr. 1992).

Kaban et al., "Treatment of Jaw Defects with Demineralized Bone Implants", *Journal of Oral and Maxillofacial Surgery*, pp. 623-626 (Jun. 6, 1989).

Kasten et al., "Comparison of Human Bone Marrow Stromal Cells Seeded on Calcium-Deficient Hydroxyapatite, Betatricalcium Phosphate and Demineralized Bone Matrix", *Biomaterials*, 24(15):2593-603 (2003).

Katz, "The Biology of Heavy Water," *Scientific American*, 106-116 (1960).

Kawai et al., *Clin. Orthopaedics and Related Res.*, 233: 262-267 (1988).

Krysan, D.J., et al., "Quantitative Characterization of Furin Specificity", *Journal Biol. Chem.* 274, pp. 23229-23234 (1999).

Kubler et al. "Allogenic Bone & Cartilage Morphogenesis," *J. Craniomaxillofac. Surg.*, 19(7): 283-288 (1991).

Kubler et al. "Osteoinductive, morphologic, and biomechanical properties of autolyzed, antigen-extracted, allogeneic human bone," *J. Oral Maxillofac Surg*, 51: 1346-1357 (1993).

Kubler et al. "Repair of human skull defects using osteoinductive bone alloimplants," *J. of Cranio Maxillofac. Surg.* 23: 337-346 (1995).

Lee et al., *Nature*, 424: 389 (2003).

Lewandrowski et al., "Flexural Rigidity in Partially Demineralized Diaphyseal Bone Grafts", *Clin, Ortho. Rel. Res.*, 317: 254-262 (1995).

Lewandrowski et al. "Improved Osteoinduction of Cortical Bone Allografts: A Study of the Effects of Laser Perforation and Partial Demineralization" *J. Orthop. Res*. vol. 15(5): 748-756 (1997).

Lewandrowski et al. "Kinetics of cortical bone demineralization: Controlled demineralization—a new method for modifying cortical bone allografts", *Journal of Biomedical Materials Research*, vol. 31: 365-372 (1996).

Lewandrowski et al. "Mechanical Properties of Perforated and Partially Demineralized Bone Grafts," *Clin. Ortho. and Related Research*, 353: 238-246 (1998).

Lewandrowski et al., "An Electron Microscopic Study on the Process of Acid Demineralization of Cortical Bone," *Calcified Tissue Int.* 61:294-297 (1997).

Lieberman, et al. "Treatment of Osteonecrosis of the Femoral Head with Core Decompression and Human Bone Morphogenetic Protein," *Clin. Ortho. and Related Research*, 429: 139-145. (2004).

Lotz, *Clin. Orthopaedics and Related Res.*, 391S: S108-S115 (2001).

Mellonig, James. "Bone Allografts in Periodontal Therapy," *Clin. Ortho. and Related Research*, 324: 116-125 (1996).

Mellonig, "Decalcified freeze-dried bone allograft as an implant material in human periodontal defects," *The Int'l Journal of Periodontics and Restorative Dentistry*, pp. 41-45 (1984).

Miloslav et al., "Autolyzed antigen-extracted allogeneic bone for bridging segmented diaphyseal bone defects in rabbits," *Clinical Orthopaedics and Related Research*, 229: 249-256 (Apr. 1988).

Nade et al. "Decalcified Bone as a Substrate for Osteogenesis," *Bone Joint Surg.* 59(2): 189-1996 (1977).

Nogami et al., "Sustrata Prepared from Bone Matrix for Chondrogenesis in Tissue Culture", *The Journal of Cell Biology*, 62: 510-519 (1974).

Nogami et al., "Transmembrane Bone Matrix Gelatin—Induced Differentiation of Bone", *Calcif. Tiss. Res.*, 19: 153-163 (1975).

Oberg et al. "Bone formation after implantation of autolysed antigen extracted allogeneic bone in ovariectomized rabbits," *Int. J. Oral Maxillofac. Surg.* 32: 628-632 (2003).

Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114 (1994).

"Organic Reactions", vols. 1-40, John Wiley and Sons, New York, NY (1991).

Ousterhout. "Clinical Experience in Cranial and Facial Reconstruction with Demineralized Bone," *Ann. Plast. Surg.* 15(5): 367-373 (1995).

Paralkar et al., "An EP2 receptor-selective prostaglandin $E_2$ agonist induces bone healing," *PNAS*, 100(11): 6736-6740 (2003).

Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).

Ray et al., "Bone Implants," *J. Bone Joint Surgery*, 39A(5): 1119-1128 (1957).

Reddi et al., "Biochemical Sequences in the Transformation of Normal Fibroblasts in Adolescent Rats," *Proc. Natl. Acad. Sci. USA*, 69(6): 1601-1605 (1972).

Ripamonti et al. "Bone induction in a composite allogeneic bone/alloplastic implant," J. *Oral Maxillofac. Surg.* 47: 963-969 (1989).

Ripamonti et al. "The induction of bone in osteogenic composites of bone matrix and porous hydroxyapatite replicas: Experimental study on the baboon," *Oral Maxillofac. Surg.* 9: 817-830 (1991).

Ripamonti. "Bone induction in nonhuman primates: an experimental study on the baboon," *Clin. Ortho. and Related Research*, 269: 284-294 (Aug. 1991).

Ripamonti. "Calvarial regeneration in primates with autolyzed antigen-extracted allogeneic bone," *Clin. Ortho. and Related Research*, 282: 293-303 (Sep. 1992).

Rodd, "Chemistry of Carbon Compounds", vols. 1-5 and supplementals, Elsevier Science Publishers, Amsterdan (1989).

Ronningen et al. "Bone formation enhanced by induction," *Acta Orthop Scan* 56: 67-71 (1985).

Ronningen et al. "Osteogenesis promoted by bone matrix combined with marrow," *Acta Orthop Scand* 5Z: 15-18 (1986).

Rosenquist et al. "Effects of bone grafting on maxillary bone healing in the growing pig," *J. Oral Maxillofac. Surg.* 40: 566-569 (1982).

Rosenthal et al. "Demineralized bone implants for nonunion fractures, bone cysts, and fibrous lesions," *Clin. Ortho. and Related Research* 362: 61-69 (1999).

Russell et al., "Clinical Utility of Demineralized Bone Matrix for Osseous Defects, Arthrodesis, and Reconstruction; Impact of Processing Techniques and Study Methodology," *Orthopaedics*, 22(5): 524-531 (May 1999).

Sailer et al. "Application of purified bone morphogenetic protein (BMP) in cranio-maxillo-facial surgery," *Jour. of Cranio-Maxillo-Facial Surgery* 22: 2-11 (1994).

Sambrook, et al. Molecular Cloning: A Laboratory Manual, $3^{rd}$ ed., Cold Spring Harbor Laboratory Press, Cold Spring Harbor (2001).

Sampath and Reddi, "Homology of bone-inductive proteins from human, monkey, bovine, and rat extracellular matrix," *Proc. Nat. Acad. Sci.* 80:6591-6594 (1983).

Sampath et al., "Bovine osteogenic protein is composed of dimmers of OP-1 and BMP-2A, Two members of the transforming growth factor-beta superfamily,"*J. Biol. Chem.*, 5:265(22): pp. 13198-13205 (Aug. 1990).

Sampath et al., "Isolation of osteogenin, an extracellular matrix-associated, bone-inductive protein, by heparin affinity chromatography," *Proc. Natl. Acad. Sci.* 84(7): 7109-7113 (1987).

Schmid et al. "Osteoinduction in tibial defects in the dog," Unfallchirurgie 19: 1-8 (1993).

Schwarz et al., "Dog bone less osteogenetic than rat bone," *Acta. Orthop. Scan.* 60(6): 693-695 (1989).

Schwarz et al. "Decalcified and undecalcified cancellous bone block implants do not heal diaphyseal defects in dogs," *Arch. Orthop. Trauma Surg.* 111:47-50 (1991).

Serini et al., "Class 3 semaphorins control vascular morphogenesis by inhibiting integrin function," *Nature*, 424:391-397 (Jul. 2003).

(56) References Cited

OTHER PUBLICATIONS

Smith, Michael et al. "March's Advanced Organic Chemistry", 5<sup>th</sup> edition, John Wiley and Sons, New York, NY (Mar. 2001).

Steadman et al., "Microfracture: Surgical Technique and Rehabilitation to Treat Chondral Defects", *Clin. Orthop.*, 391 S:362-369 (2001).

Steiner, D.F., "The proprotein convertases," *Curr. Opinion Chem. Biol.* 2: 31-39 (1998).

Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).

Terashima et al., Chondrogenesis in Outgrowths of Muscle Tissue onto Modified Bone Matrix in Tissue Culture, *Clinical Orthopaedics and Related Research*, 127: 248-256 (Sep. 1977).

Todescan et al., "A Small Animal Model for Investigating Endosseous Dental Implants: Effect of Graft Materials on healing of Endoss, Porous-Surfaced Implants Placed in a Fresh Extraction Socket," *The Journal of Oral and Maxillofacial Implants*, 2(2): 217-223 (1987).

Toriumi et al. "Demineralized Bone," Arch Otolaryngol Head Neck Surg. 116: 676-680 (Jun. 1990).

Ueland et al., *J. Clin. Endocrinol. & Metab.*, 84(1): 123-127 (1999).

Urist et al., "Bone morphogenesis in Implants of Insoluble Bone Gelatin," *Proc. Natl. Acad. Sci.*, , 70(12): 3511-5 (Dec. 1973).

Urist et al., ., "Preservation and biodegradation of the morphogenetic property of bone matrix," *J. Theor. Biol.* 38: 155-67 (1973).

Urist et al., "Observations implicating an extracellular enzymic mechanism of control of bone morphogenesis," *J. Histochem & Cytochem*, 22(2): 88-103 (1974).

Urist et al., "A Chemosterilized Antigen-Extracted Autodigested Alloimplant for Bone Banks," *Arch Surg.* vol. 110: 416-428 (Apr. 1975).

Urist et al., "Cartilage Tissue Differentiation from Mesenchymal Cells Derived from Mature Muscle in Tissue Culture", *In Vitro*, 14(8): 697-706 (1978).

Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).

Urist et al., "Human Bone Morphogenetic Protein (hBMP)," *Proc. Soc. Exp. Biol.* 173:194-199 (1983).

Urist et al., "Purification of bovine bone morphogenetic protein by hydroxyapatite chromatography," *Prop. Natl. Acad. Sci.* 81:371-375 (1984).

Van den Berg et al., "Tissue Engineering, Cells, Scaffolds, and Growth Factors," *Clin. Orthopaedics and Related Res.*, 391S: S244-S250 (2001).

Van den Ouweland, A.M.W. et al., "Structural homology between the human *fur* gene product and the subtilisin-like protease encoded by yeast *KEX2*," *Nucl. Acid Res.* 18(3): 664 (1990).

Wang et al., "Purification and characterization of other distinct bone-inducing factors," *Proc. Nat. Acad. Sci.* 85:9484-9488 (1988).

Wang et al., "Recombinant human bone morphogenetic protein induces bone formation," *Proc. Nat. Acad. Sci.* 87:2220-2224 (1990).

Whittaker et al., "Matrix Metalloproteinases and Their Inhibitors—Current Status and Future Challenges," *Celltransmissions*, 17(1): 3-14. Feb. 2001.

Wise, D.L., "Encyclopedia Handbook of Biomaterials and Bioengineering Part B", Applications New York: Marcel Decker (1995).

Young et al. "Morphological changes of autoclaved autogenic bone implantation and autoclaved autogenic bone supplemented with allogenic demineralized bone matrix in rat parietal bone," *Histol Histopathol.* 11: 361-369 (1996).

Zhang et al., "A Quantitative assessment of osteoinductivity of human demineralized bone matrix," *J. Periodontal*, 68(11): 1076-84 (Nov. 1997).

\* cited by examiner

Lyophilization

CPD

CPD (44°C, 1400psi)

SC-CO$_2$ (105°C, 7000psi)

METHOD OF TREATING BONE TISSUE

CROSS-REFERENCED TO RELATED APPLICATION(S)

This application claims benefit of priority to U.S. Ser. No. 60/944,408 filed on Jun. 15, 2007, the contents of which are incorporated herein by reference.

FIELD

Methods of treating tissue that promote remodeling and replacement by host tissue are provided. More particularly, methods of treating tissue for sterilization or drying are provided.

BACKGROUND

Overview of Bone Grafts

The rapid and effective repair of bone defects caused by injury, disease, wounds, or surgery has long been a goal of orthopaedic surgery. Bone grafting is a well established surgical technique. Sources of bone are autograft (primarily from cancellous bone sources), allograft (generally comprising cancellous bone and structural cortical pieces), and xenograft (typically cancellous bone). With any bone graft, it is advantageous for the graft to integrate quickly with the host bone and then to be remodeled into host bone. In structurally loaded graft sites, it is desired that the bone graft integrate while maintaining its strength throughout the remodeling process.

Several compositions and materials have thus been used or proposed for use in the repair of bone defects. The biological, physical, and mechanical properties of the compositions and materials are among the major factors influencing their suitability and performance in various orthopaedic applications. Desirably, materials used for the repair of bone defects are remodeled—the material being resorbed and replaced by similar host tissue. For example, implanted bone being replaced by host bone.

Bone, both cortical and cancellous, has been used in the repair of bone defects. As will be discussed, bone remodeling, including resorption of the implanted bone material and formation of new bone material, is desirable for implanted bone material. Reference is thus made to resorption rates as a guide to rates of remodeling. Cortical bone is stronger than cancellous bone but is not resorbed or remodeled as quickly as cancellous bone. Complete remodeling of cortical bone may take ten or more years. Consequently, many surgeons prefer cancellous bone for bone grafting. However, because cancellous bone does not have the strength of cortical bone, it is not suitable for all applications.

Cortical bone comprises approximately 70% mineral, 20% protein (primarily Type 1 structural collagen), and 10% water. The mineral comprises very small (nanoscale) crystals of impure hydroxyapatite. These crystals have a large surface area and are reasonably resorbable. However, in cortical bone, the collagen structure is dense and acts as a limiting factor in resorption. The resorption rate of the collagen structure is limited by the fact that initial degradation occurs only by the action of the specific enzyme collagenase.

Resorption of cancellous bone is generally faster than resorption of cortical bone. Among other things, pores in the cancellous bone allow cells to infiltrate and grow new bone, while providing a large surface area for enzymatic attack to occur on the collagen.

Much effort has been invested in the identification and development of bone graft materials, including treating bone for such use. Urist has published seminal articles on the theory of bone induction and a method for decalcifying bone, i.e., making demineralized bone matrix (DBM). Urist M. R., Bone Formation by Autoinduction, Science 1965; 150(698): 893-9; Urist M. R. et al., The Bone Induction Principle, Clin. Orthop. Rel. Res. 53:243-283, 1967. DBM is an osteoinductive material, in that it induces bone growth when implanted in an ectopic site of a rodent, owing to the osteoinductive factors contained within the DBM.

DBM implants have been reported to be particularly useful (see, for example, U.S. Pat. Nos. 4,394,370, 4,440,750, 4,485, 097, 4,678,470, and 4,743,259; Mulliken et al., *Calcif Tissue Int.* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993, each of which is incorporated herein by reference). DBM typically is derived from cadavers. The bone is removed aseptically and treated to kill any infectious agents. The bone may be particulated by milling or grinding, and then the mineral component is extracted by various methods, such as by soaking the bone in an acidic solution. The remaining matrix is malleable and can be further processed and/or formed and shaped for implantation into a particular site in the recipient. Demineralized bone prepared in this manner contains a variety of components, including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

Many of the processes used to prepare tissue for transplant cause some collagen damage. These processes include, for example, treatment with oxidizing agents such as peroxides, irradiation, and autoclaving. While limited collagen damage to the tissue may increase the rate of bone remodeling, too much collagen damage (as often occurs from such treatments) leads to replacement of the tissue with undesirable fibrous tissue.

Overview of Collagen

Collagen is the major component of extracellular matrix (ECM) of many tissues including bone, tendon, ligament, skin and others. Collagen is organized in fibrillar bundles. In tissue, the organization of collagen matrix is essential for the mechanical properties. In addition, the oriented fibrillar structure of collagen facilitates cellular recognition and provides a suitable carrier for many biological active molecules such as growth factors including BMPs. It has been demonstrated to be important for cell attachment, proliferation, differentiation, and remodeling or reorganization. In processing of tissue grafting materials, in some specific applications, it may be desirable that the natural collagen structures are preserved.

Overview of Bone Sterilization and Bone Remodeling

It is generally desirable that bone grafts be free of disease causing pathogens such as viruses, bacteria, mold, fungus, and yeast. Viruses are a specific type of pathogen. Viruses are active inside cells but not in the general environment. If viruses are present in bone graft material, then they were present in the tissue before harvest. Once viruses are inactivated, it is unlikely that the tissue will become recontaminated with viruses. This is in contrast to bacteria, mold, etc., which can readily recontaminate tissue unless special precautions are taken to surround the tissue with a sterile barrier or process it in a sterile environment.

To ensure that the tissue is free of pathogens, the tissue is typically screened for possible diseases, may be processed aseptically, and additional cleaning/disinfecting steps may be carried out. Pathogen inactivation or removal depends on various factors including temperature, pressure, time, and the use of chemical agents. Collagen damage may result from pathogen inactivation processes. Examples of collagen damaging sterilization/viral inactivation techniques include treatment with harsh oxidizing agents, radiation, or autoclaving. Other pathogen inactivation processes, such as detergent or alcohol rinses, cause little or no collagen damage.

Supercritical, critical or near critical fluids have been used to remove or inactivate virus or virus-like particles (U.S. Pat. No. 5,877,005; U.S. Pat. No. 6,217,614 B1; U.S. Pat. No. 7,008,591; White et al., J. Biotech. 123:504, 2006). These methods generally apply supercritical fluids with other chemical agents, or apply supercritical fluids at relatively low temperature such as below 60° C., or apply supercritical fluids to a solution of a biological material. Treatment with supercritical fluids at lower temperature does not always inactivate all pathogens, especially non-enveloped viruses. On the other hand, the use of chemical agents may destroy the biological activity of the materials such as bone grafting materials.

Bone remodeling is a dynamic process by which old bone is removed from the skeleton and new bone is added. Bone remodeling comprises two stages: resorption and formation. One method of improving bone remodeling is to degrade collagen to facilitate the resorption stage of bone remodeling.

Accordingly, pathogen inactivation processes that cause collagen damage may increase the rate of bone resorption. This may not, however, lead to bone remodeling. The collagen damage sometimes can result in the bone being replaced by undesirable fibrous tissue instead of bone. Bone that has been subjected to harsh treatments, such as autoclaving or high radiation doses, to sterilize the bone often resorbs quickly but is not replaced by host bone. These harsh treatments break down collagen in the bone but do so in a way that the implanted bone often causes chronic inflammation—the implanted bone having been replaced by fibrous tissue. For this reason, sterilization/viral inactivation treatments that damage collagen are generally limited in their time or harshness (low peroxide concentrations, low radiation doses, etc.) in order to reduce collagen damage. While such limiting does reduce collagen damage, it also compromises the effectiveness of the treatments.

Thermal treatment of bone, for example by autoclaving or using dry heat, for sterilization is not typically done. Bone that has been sterilized by these techniques is generally found to be resorbed but not remodeled. Thus, while heating is simple, rapid, and leaves no chemical residues, the lack of remodeling following implantation of graft material has made it largely undesirable.

It would be useful to have a method of sterilization without substantially degrading biological properties of the bone.

BRIEF SUMMARY

A method of treating tissue that promotes remodeling and replacement by host tissue is provided. More particularly, in some embodiments, a method of degrading collagen in bone is provided.

In one embodiment, the method comprises providing tissue, preparing the tissue, and heating the tissue in the absence of oxygen. Heating the tissue in the absence of oxygen may comprise heating the tissue in a vacuum, heating the tissue in an inert atmosphere, heating the tissue in a reducing atmosphere, coating the tissue with a protective coating and heating the bone, or other suitable manner of heating the bone in the absence of oxygen.

In another embodiment, the method comprises providing cortical bone, preparing the cortical bone, and treating the cortical bone to disrupt collagen structure of the cortical bone. After such treatment, the cortical bone retains at least approximately 30% of its original strength.

In yet another embodiment, a tissue-based material treated to improve its remodeling characteristics is provided. The tissue-based material may comprise bone, tendon, skin, musculoskeletal tissue, or other soft tissue. Treatment may comprise heating the tissue, for example in the absence of oxygen, treating tissue with a chemical, or other. The tissue may be prepared prior to treatment by, for example, removing lipids or water from the tissue.

In a further embodiment, the method includes treating tissue in a supercritical fluid. The method may be used to dry the tissue or to virally inactivate the tissue.

While multiple embodiments are disclosed, still other embodiments of the present invention will become apparent to those skilled in the art from the following detailed description. As will be apparent, the method disclosed herein is capable of modifications in various obvious aspects, all without departing from the spirit and scope of the present teachings. Accordingly, the detailed description is to be regarded as illustrative in nature and not restrictive.

DEFINITIONS

Figure 1:
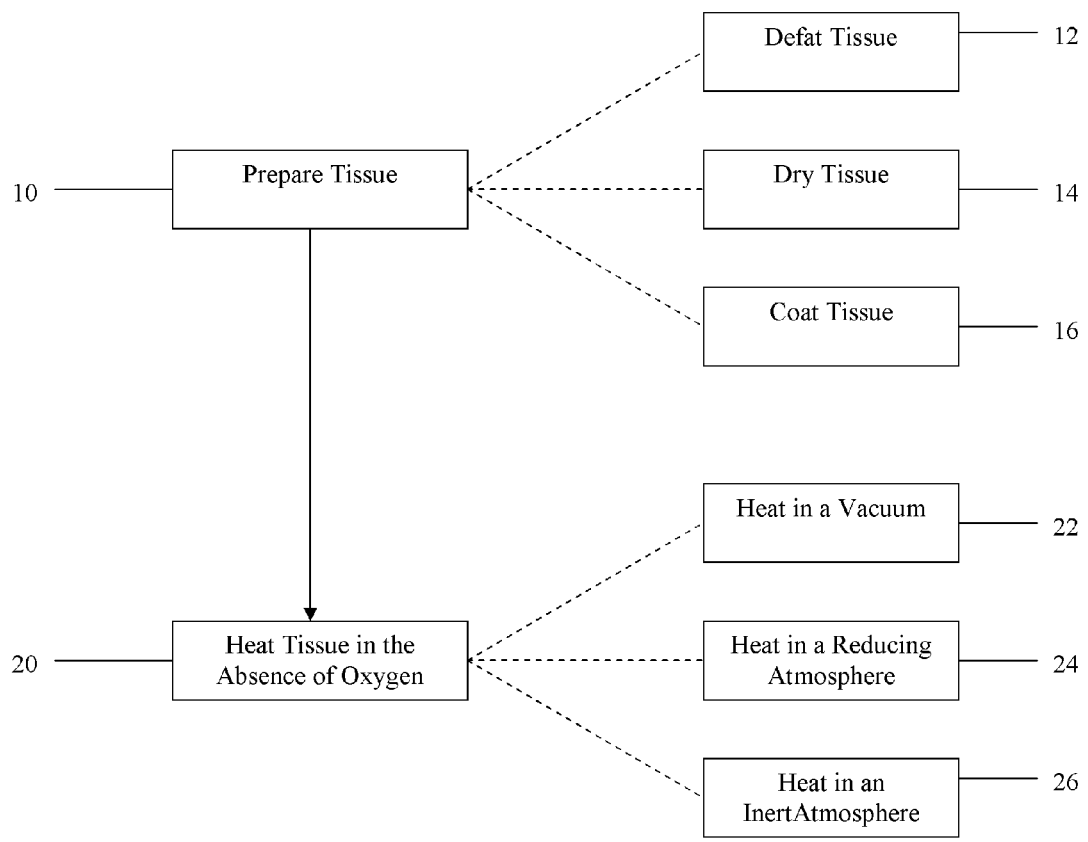
FIG. 1 illustrates a flow chart of a method of treating tissue in accordance with one embodiment.

Biocompatible, as used herein, refers to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized bone, as used herein, refers to material generated by removing mineral material from bone tissue. The DBM compositions as used herein may include preparations containing less than 5% calcium, or less than 1% calcium by weight. Partially demineralized bone (e.g., preparations with greater than 5% calcium by weight but containing less than 100% of the original starting amount of calcium) are also considered within the scope of the present teachings. Superficially demineralized refers to bone-derived elements possessing at least about 90 weight percent of their original inorganic mineral content. Partially demineralized refers to bone-derived elements possessing from about 8 to about 90 weight percent of their original inorganic mineral content. Fully demineralized refers to bone containing less than 8% of its original mineral context. Demineralized bone encompasses such expressions as "substantially demineralized," "partially demineralized," "surface demineralized," "superficially demineralized," and "fully demineralized."

Denature, as used herein, refers to change of physical structure of a protein without change to its chemical composition.

Digestion, as used herein, refers to the breaking down of a protein into small units.

Inflammation, as used herein, refers to the first response of the immune system to infection or irritation. Inflammation refers to a tissue reaction characterized by the presence of multinucleated giant cells without infection being present.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoinductive, as used herein, refers to the quality of being able to recruit cells from the host that have the potential to stimulate new bone formation. Any material that can induce the formation of ectopic bone in the soft tissue of an animal is considered osteoinductive. In other instances, osteoinduction is considered to occur through cellular recruitment and induction of the recruited cells to an osteogenic phenotype.

Proteases, as used herein, refer to protein-cleaving enzymes that cleave peptide bonds that link amino acids in protein molecules to generate peptides and protein fragments. A large collection of proteases and protease families has been identified. Some exemplary proteases include serine proteases, aspartyl proteases, acid proteases, alkaline proteases, metalloproteases, carboxypeptidase, aminopeptidase, cysteine protease, collagenase, etc. An exemplary family of proteases is the proprotein convertase family, which includes furin. Dubois et al., *American Journal of Pathology* (2001) 158(1):305316. Members of the proprotein convertase family of proteases are known to proteolytically process proTGFs and proBMPs to their active mature forms. Dubois et al., *American Journal of Pathology* (2001) 158(1):305-316; Cui et al., *The Embo Journal* (1998) 17(16):4735-4743; Cui et al., *Genes & Development* (2001) 15:2797-2802, each incorporated by reference herein.

Remodeling, as used herein, refers to a process by which implanted tissue is replaced by similar host tissue. Bone remodeling comprises two stages: resorption and formation.

Resorption, as used herein, refers to a process by which the implanted tissue is resorbed by the body and effectively disappears. Resorption may be the first stage of remodeling if followed by formation of host tissue similar to the implanted tissue. If followed by replacement by other tissue, such as fibrous tissue, remodeling is not achieved.

Supercritical fluid, as used herein, refers to a substance at a temperature and pressure above its thermodynamic critical point. Under these conditions, the distinction between gases and liquids does not apply and the substance is described as a fluid. Under these conditions, a supercritical fluid has the ability to diffuse through solids like a gas, and dissolve materials like a liquid. Additionally, a supercritical fluid can readily change in density upon minor changes in temperature or pressure.

Supercritical carbon dioxide, as used herein, refers to carbon dioxide ($CO_2$) above its thermodynamic critical point (i.e., above critical temperature of 31.1° C. and pressure of 1100 psi). Supercritical carbon dioxide is an excellent nonpolar solvent for many organic compounds. It has been likened to a solvent resembling hexane, though with some hydrogen-bonding acceptor capability and some dipole selectivity. Alkenes, alkanes, aromatics, ketones, and alcohols (up to a relative molecular mass of around 400) dissolve in supercritical carbon dioxide. Very polar molecules such as sugars or amino acids and most inorganic salts are insoluble. By adjusting the pressure of the fluid, the solvent properties can be adjusted to more "gas-like" or more "liquid-like", which allows tuning of the solvent properties.

DETAILED DESCRIPTION

A method of treating tissue that promotes remodeling and replacement by host tissue is provided. In accordance with methods provided herein, the tissue may be damaged such that, after implantation, the body can recognize and repair the damage. More particularly, in accordance with certain embodiments of the methods taught herein, the collagen structure of tissue is altered or degraded, resulting in surface damage that cells can recognize in vivo. In some embodiments, the collagen degradation further acts to reduce the pathogen load in the tissue and thus performs sterilization or viral inactivation functions. In further embodiments, the tissue is dried using critical point drying, for example with supercritical carbon dioxide. In yet further embodiments, the tissue undergoes viral inactivation by treatment with supercritical fluids, such as supercritical carbon dioxide. Various of these methods further may be combined in treating tissue.

In some embodiments, the methods may be applied to bone, such as cortical bone. While the discussion herein focuses primarily on bone (mineralized, demineralized, or partially demineralized), the method may alternatively be used to treat other tissues including other bone-derived components, soft tissue such as tendons and ligament grafts, cartilage, fascia, musculoskeletal tissues, skin, organ tissues, and others, as well as the combination of those or the combination of a tissue material and a carrier material.

The tissue treated in accordance with the methods disclosed herein may be obtained utilizing methods well known in the art, e.g., allogenic donor tissue. The tissue may be of autogenous, allogenic, xenogenic, or transgenic origin. Bone-derived elements can be readily obtained from donor bone by various suitable methods, e.g., as described in U.S. Pat. No. 6,616,698, incorporated herein by reference.

I. Introduction

Bone is made up principally of cells, and also of collagen, minerals, and other noncollagenous proteins. Cortical bone, which accounts for approximately eighty percent of skeletal bone mass, is found in the hard outer layer of bone. Cortical bone is structural and bears the majority of the body's weight. Cancellous bone is the porous and spongy inner structure accounting for approximately twenty percent of skeletal bone mass. Cancellous bone contains bone marrow and the elements required for bone to heal itself.

Cortical bone is stronger than cancellous bone but is not resorbed or remodeled as quickly as cancellous bone. Complete remodeling of cortical bone may take ten or more years.

II. Overview Of Degrading Collagen In Tissue

In accordance with one embodiment, a method provided herein comprises degrading collagen in tissue in a manner that does not lead to inflammatory tissue response when the tissue is implanted and promotes remodeling and replacement by the host tissue. In some embodiments, methods provided herein may be applied to cortical bone Cortical bone grafts treated in accordance with some of the embodiments provided herein generally remodel faster than untreated bone, and retain strength in excess of that of cancellous bone. In some embodiments, bone treated as provided herein is substantially sterilized.

Some embodiments provided herein disrupt the collagen structure in tissue to enhance bone remodeling. Disruption of the collagen structure may be done in any suitable manner including, for example, heat treatment, chemical treatment, mechanical treatment, energy treatment (e.g., x-ray or radiation), and others. The collagen structure of bone comprises a triple helix form. Bone may be treated such that the triple helix form unwinds but covalent crosslinks of the structure remain intact. In general, the treatment is such that the collagen in the bone is denatured or digested to the point where protease enzymes can readily attack it, while at the same time avoiding the creation of toxic byproducts, and maintaining some of the original strength of the bone.

More specifically, collagen consists of fibrils composed of laterally aggregated, polarized tropocollagen molecules (MW 300,000). Each tropocollagen unit consists of three helically wound polypeptide $\alpha$-chains around a single axis. The strands have repetitive glycine residues at every third position and numerous proline and hydroxyproline residues, with the particular amino acid sequence being characteristic of the tissue of origin. Tropocollagen units combine uniformly to create an axially repeating periodicity. Cross linkages continue to develop and collagen becomes progressively more insoluble and resistant to lysis on aging. Gelatin results when soluble tropocollagen is denatured, for example on mild heating, and the polypeptide chains become randomly dispersed. In this state the strands may readily be cleaved by a wide variety of proteases.

Various methods for disrupting the collagen structure of tissue may be used. For example, heat treatment, treatment with collagenase, other chemical treatment, mechanical treatment, or energy treatment may be employed. In some embodiments, these methods may be applied to demineralized bone. U.S. patent application Ser. No. 12/140,044, to Bone Matrix Compositions and Methods, filed Jun. 16, 2008 and U.S. patent application Ser. No. Osteoinductive Demineralized Cancellous Bone, filed Jun. 16, 2008, are both herein incorporated by reference in their entireties for the purposes of all that is disclosed therein.

III. Thermal Treatment of Tissue

In some embodiments, the method herein comprises thermal treatment of tissue. Thermal treatment of tissue is simple, rapid, and leaves no chemical residues. In the past, techniques for performing thermal treatment of tissue have resulted in tissue that, upon implantation, is resorbed but not remodeled. Traditional methods of heating or autoclaving are damaging at least because these processes are carried out in air, allowing oxygen to react at the treatment temperature to form new breakdown species that do not occur in a natural degradation process. These oxygenated fragments are suspected to be the cause of the often observed inflammatory response. Accordingly, in some embodiments, the conditions under which heating is carried out are selected such that thermal treatment may serve to inactivate viruses, sterilize tissue, and yet also promote remodeling.

One embodiment thus may comprise heat sterilizing tissue, such as bone, without substantially degrading biological properties of the tissue. The biological properties of the tissue may be not substantially degraded, left substantially intact, or improved. In some embodiments, the method comprises gentle heating of the tissue. In another embodiment, the method comprises heating the tissue in the absence of oxygen. In a further embodiment, the method comprises heating the tissue in the presence of supercritical $CO_2$.

Thus, in a first embodiment, gentle heating of the tissue is performed to denature proteins in the tissue. Heating may be performed, for example, at temperatures of approximately 70° C. Gentle heating generally does not chemically degrade the proteins in the tissue. Such gentle heating limits potential inflammatory response. In another embodiment, the tissue may be defatted before the heat treatment to remove lipids, which are a potential thermal peroxygen compound source. Using gentle heating and/or defatting, other steps may be performed for pathogen inactivation.

In general, the kinetics of pathogen inactivation is an exponential function of temperature. Thus, a temperature of 100° C. will inactivate pathogens in a fraction of the time needed at a lower temperature such as 60° C., and complete destruction of pathogens, including viruses, is practical at temperatures of approximately 100° C. or higher. Unfortunately, tissue that has been sterilized by autoclaving or subjected to a high temperature dry heat treatment, while safe from a pathogen point of view, tends to be resorbed without remodeling. Thus, for example, heating has not previously been a satisfactory method of sterilization of bone for bone grafting applications.

In some embodiments, the tissue may be dried, as discussed more fully below, prior to heat treatment. Drying may be done to any suitable level. For example, drying may be done to remove 50%, 75%, 80%, 90%, 95%, 98%, or 99% of the water from the tissue. Proteins are generally more thermally stable in the absence of water and, thus, the heat treatment may be carried out at higher temperatures when the tissue is dry and such higher temperatures may be beneficial for viral activation.

In one embodiment, shown in FIG. 1, tissue is heated in the absence of oxygen. The tissue is prepared prior to heating [block 10]. Such preparation may comprise cleaning, scraping, defatting, drying (for example by lyophilizing), or other. After the tissue is prepared [block 10], the tissue is heated in the absence of oxygen [block 20]. The method may be used, for example, on cortical bone. Heating in the absence of oxygen may be done in any suitable manner. For example, heating may be done using an inert atmosphere [block 26], heating may be done in a reducing atmosphere [block 24], heating may be done in a vacuum [block 22], heating may be done in a shielding coating [block 16] (providing the coating over the tissue being done during preparation of the tissue at block 10), or other means. In embodiments wherein cortical bone is heated in the absence of oxygen, the cortical bone has a faster remodeling time and retains strength at least equal to that of cancellous bone. Generally, cortical bone so treated possesses at least about 30% of its original strength In some embodiments, heating conditions may be selected such that they will result in virally inactivated tissue. For example, the bone may be heated at temperatures of approximately 100° C. or more, in the absence of oxygen. The treated tissue may be implanted either as is, or with additional materials such as a polymer matrix, antibiotics, growth factors, physical property modifiers such as glycerol, or any combination of these materials. In addition, in embodiments wherein bone is treated, the bone may be demineralized either fully or partially after the heat treatment.

In some embodiment of heating in the absence of oxygen, the tissue is heated in an inert atmosphere [block 26] or heated in a reducing atmosphere [block 24]. Such atmosphere acts as a protective atmosphere. Inert atmospheres may include argon, nitrogen, helium, $CO_2$ (including supercritical $CO_2$), a hydrocarbon vapor, mixtures of these gases, etc. Reducing atmospheres may comprise a reducing gas such as pure hydrogen or hydrogen mixed with an inert gas wherein the atmosphere comprises between 1 and 99 percent hydrogen. Using a reducing gas, reductive free radicals, for example from hydrogen, are produced to protect against the effects of oxidative free radicals. In various embodiments, the tissue may be treated in a chamber wherein the protective atmosphere is introduced to the chamber and released after treatment. The method of release of the atmosphere may be controlled to affect the tissue. For example, slow release of the atmosphere has little effect on the tissue. In contrast, fast release of the atmosphere may cause the tissue to expand and develop pores.

Another embodiment of heating in the absence of oxygen comprises heating the tissue in a vacuum [block 22].

Yet a further embodiment of heating in the absence of oxygen comprises coating the tissue with a protective thermal coating [block 16] and heating the coated tissue. The protective thermal coating forms an oxygen barrier and, thus, the tissue with the protective thermal coating may be heated in an oxygenated atmosphere. Such protective thermal coatings may comprise, for example, a polymer or wax that does not react with the tissue and that forms an oxygen barrier. In one embodiment, the protective coating comprises PolyDTE polymer. In another embodiment, the protective coating comprises a mix of Poly (lactide-co-glycolide) and Poly(ethylene glycol). The protective coating may be layered over a monolithic piece of tissue or may be mixed with tissue granules—such as particulated bone. When mixed with particulated bone, for example, the polymer/bone mix may be molded to form an implant.

In some embodiments, the tissue is heated in the presence of oxygen, for example, wherein the tissue is protected from effects of the presence of oxygen by providing a coating over the tissue. In some embodiments, the tissue is heated as part of a molding process. For example, in some embodiments, the tissue may be admixed with a polymer, the tissue and polymer mixture placed in a mold, and the mold heated. Reference is made to U.S. Pat. No. 6,696,073, U.S. Pat. No. 6,478,825, U.S. Pat. No. 6,440,444, U.S. Pat. No. 6,294,187, U.S. Patent Publication No. 2006/0216323, and U.S. Patent Publication No. 2005/0251267, all herein incorporated by reference for discussion of bone particle containing aggregates that may be molded.

Returning to block 10 of FIG. 1, in some embodiments, the tissue is prepared prior to heating. More specifically, in some embodiments, internal substances that may react at the heat treatment temperature may be removed before heating. Such internal substances may comprise water and lipids. Water can hydrolyze collagen to form acidic products during heating. Thus, treating the tissue may comprise removing water from the tissue, partially or completely. Regardless of the amount of water removed, this may be referred to as drying the tissue. Such drying may be beneficial when a dry heat process is used. Drying may comprise lyophilization, vacuum drying, solvent dying, or other drying. Dry heat is easier to maintain in an oxygen-free environment. Further, a dry heat treatment is potentially less damaging to the tissue because the potential for producing acid hydrolysis products is reduced. The tissue may be further dried after thermal treatment to remove residual water.

Removing lipids before thermal treatment may also be done and generally reduces or eliminates another source of reactive oxygen. Lipids can oxidize and cause oxidative cross-linking during heating. Accordingly, in some embodiments, lipid removal may be prior to thermal treatment. Defatting may be done in any suitable manner such as using known solvent based techniques. For example, defatting may be done using supercritical $CO_2$, chloroform-methanol, acetone, alcohol, or others.

Combinations of treatments designed to degrade collagen can be used; for example, a mild heating combined with an enzyme or base treatment; or an enzyme treatment followed by a radiation treatment. Any suitable combination of treatments, including treatments not discussed herein, may be used.

IV. Chemical Treatment

Another method of degrading collagen in tissue comprises chemical treatment of the tissue. Accordingly, in accordance with some embodiments, treating the tissue to degrade the collagen structure comprises treating the tissue with a chemical wherein the chemical cleaves one or more of the three chains of the collagen helix. In some embodiments, the chemical cleaves Type I collagen, e.g., degrades the helical regions in native collagen, preferentially at the Y-Gly bond in the sequence Pro-Y-Gly-Pro-, where Y is most frequently a neutral amino acid. This cleavage yields products susceptible to further peptidase digestion. Any chemical or protease having one or more of these activities may be used to treat the tissue.

In one embodiment, the tissue is treated with a collagenase enzyme. Generally, when tissue is treated with collagenase, natural degradation products are formed. Where the tissue comprises bone, because the dense structure of the bone that inhibits remodeling may complicate an enzyme treatment process, getting the enzyme to penetrate the bone can be difficult. Physical methods such as centrifugation in an enzyme solution, or the use of a solvent such as DMSO, may thus be used.

Collagenases and their activity on collagens of various types have been extensively studied. A number of collagenase preparations are available from Worthington Biochemical Corporation, Lakewood, N.J. In general, a variety of different collagenases known in the art can be used to disrupt the collagen structure of the bone. Collagenases are classified in section 3.4.24 under the International Union of Biochemistry and Molecular Biology (NC-IUBMB) enzyme nomenclature recommendations (see, e.g., 3.4.24.3, 3.4.24.7, 3.4.24.19). The collagenase can be of eukaryotic (e.g., mammalian) or prokaryotic (bacterial) origin. Bacterial enzymes differ from mammalian collagenases in that they attack many sites along the helix.

It will be appreciated that crude collagenase preparations contain not only several collagenases, but also a sulfhydryl protease, clostripain, a trypsin-like enzyme, and an aminopeptidase. This combination of collagenolytic and proteolytic activities is effective at breaking down intercellular matrices, an essential part of tissue disassociation. Crude collagenase is inhibited by metal chelating agents such as cysteine, EDTA, or o-phenanthroline, but not DFP. It is also inhibited by α2-macroglobulin, a large plasma glycoprotein. $Ca^{2+}$ is required for enzyme activity. Therefore, it may be desirable to avoid collagenase inhibiting agents when treating bone matrix with collagenase. In addition, although the additional proteases present in some collagenase preparations may aid in breaking down tissue, they may also cause degradation of desired matrix constituents such as growth factors. Therefore, a purified collagenase that contains minimal secondary proteolytic activities along with high collagenase activity may be used. For example, a suitable collagenase preparation may contain at least 90%, at least 95%, at least 98%, or at least 99% collagenase by weight. The preparation may be essentially free of bacterial components, particularly bacterial components that could cause inflammatory or immunological reactions in a host, such as endotoxin, lipopolysaccharide, etc. Preparations having a purity greater than 99.5% can also be used. A suitable preparation is chromatographically purified CLSPA collagenase from Worthington Biochemical Corporation. Various protease inhibitors may be included that do not inhibit collagenase but that inhibit various proteases that digest BMP. For example, protease inhibitors that are known to protect BMP activity from degradation include N-ethyl maleimide, benzamidine hydrochloride, iodoacetic acid, PMSF, AEBSF, E-64. Bestatin may also be used, particularly if the preparation contains aminopeptidase activity. Any of these protease inhibitors (or others) may be provided in a composition that is used to treat the demineralized bone.

Bone morphogenetic protein I (BMP-1) is a collagenolytic protein that has also been shown to cleave chordin (an inhibitor of BMP-2 and BMP-4). Thus, BMP-I may be of use to alter the physical structure of the demineralized bone (e.g., by breaking down collagen) and/or to cleave specific inhibitory protein(s), e.g., chordin or noggin. Proteins related to any of the proteases described herein, i.e., proteins or protein fragments having the same cleavage specificity, can also be used. It will be appreciated that variants having substantial sequence identity to naturally occurring protease can be used. For example, variants at least 80% identical over at least 50%, at least 60%, at least 70%, at least 80%, at least 90%, or 100% of the length of naturally occurring protease (or any known active fragment thereof that retains cleavage specificity) when aligned for maximum identity allowing gaps can be used.

Collagen can also be broken down by treatment with a strong base, such as sodium hydroxide. Thus, in some embodiments, sodium hydroxide can be introduced to the bone to disrupt the collagen structure of the bone. Such introduction may be in the form of a solution with penetration aided by a centrifuge and/or the addition of DMSO, as is the case for an enzyme. In embodiments wherein the tissue is bone, the base will not harm the mineral component of bone; so much of the strength (especially compressive strength) for the bone is maintained.

Other chemicals, such as cyanogen bromide, may alternatively be used to alter the collagen structure of the tissue.

Combinations of treatments designed to degrade collagen can be used; for example, a mild heating combined with an enzyme or base treatment; or an enzyme treatment followed by a radiation treatment. Any suitable combination of treatments, including treatments not discussed herein, may be used.

Further, chemical treatment may be combined with thermal treatment.

V. Critical Point Drying Using Supercritical Fluids

In some embodiments, processing tissue involves the use of critical or supercritical fluids to remove lipids and water from the tissue. The method may be used for sterilization and/or drying and may be used in lieu of alternative drying processes such as critical point drying. Air-drying typically damages tissue samples because very large surface tension forces are created when there is a liquid/gas interface. Similarly, lyophilization of tissue samples can destroy structures by ice formation and removal both at interior and exterior sites. Especially in cases of drying collagen-based tissues, air drying or lyophilization generally cause deformation and structure collapse. Drying using critical point fluids, as provided herein, substantially avoids these effects by preventing development of a liquid/gas interface. Without such interface, the tissue is not exposed to surface tension forces.

The critical point of a liquid/gas system (e.g. water/steam, liquid $CO_2/CO_2$ gas) is at its critical temperature, Tc, and the pressure associated with this temperature, Pc. Above the critical temperature, Tc, the system is always gaseous and cannot be liquefied by the application of pressure. The transition from liquid to gas at the critical point takes place without an interface because the densities of liquid and gas are equal at this point. If a tissue is totally immersed in a liquid below its critical point and the liquid is then taken to a temperature and pressure above the critical point, it is then immersed in gas without being exposed to the damaging surface tension forces.

In certain embodiments, tissues may be dried in a fluid above its critical point, referred to as critical point dying (CPD). Generally, water is not a suitable fluid for processing of biologically active tissue material because water has very high critical point (374° C., 3200 psi). Heating a biological material at such high temperature destroys its biologic activity. The present invention thus, in some embodiments, provided critical point drying of biologically active tissue materials using carbon dioxide. Carbon dioxide has relatively low critical point at 31.1° C. with corresponding pressure of 1100 psi which is relatively easy to reach and is compatible with biological materials. $CO_2$ is an excellent non-polar solvent which solubilize lipids, oil and fats in the materials. Above critical point, $CO_2$ penetrate substantially throughout the material to remove lipidic components (Fages et al, *Biomaterials*, 15:650, 1994).

Thus, in one embodiment, a method of treating tissue is provided including providing the tissue, preparing the tissue, treating the tissue in critical or supercritical fluid, and removing the tissue from the critical or supercritical fluid. Such treatment in various embodiments may be used to dry the tissue or to virally inactivate the tissue.

In certain embodiments, a $CO_2$ miscible solvent may be applied to the tissue prior to drying with $CO_2$. Specifically, water is not miscible with liquid $CO_2$ and to dry a water-containing tissue with $CO_2$-based critical point drying, a $CO_2$ miscible substitution solvent may be used to displace the water in the tissue before carrying out critical point drying. Ethanol and acetone are suitable solvents because they are miscible both with liquid $CO_2$ and water.

Figure 2:
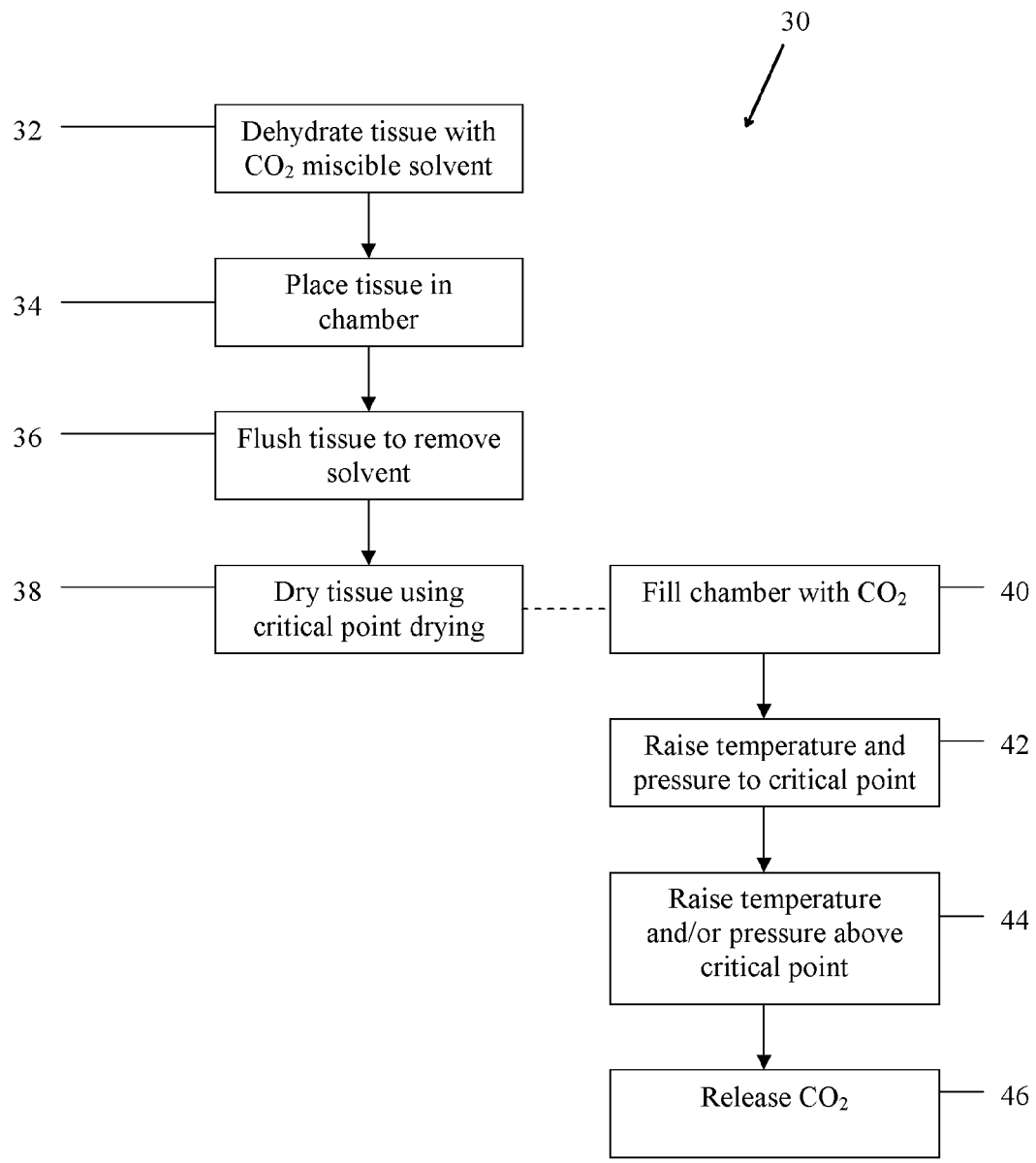
FIG. 2 illustrates a flow chart of critical point drying of tissue in accordance with one embodiment.

FIG. 2 illustrates one embodiment of a method 30 for drying a tissue using critical point drying. As shown, the method includes dehydrating the tissue with a $CO_2$ miscible solvent [block 32], placing the tissue in a chamber [block 34], flushing the tissue to remove the solvent [block 36], and drying the tissue using critical point drying [36]. Dehydrating with a the tissue with a $CO_2$ miscible solvent may comprise, for example, treating the tissue with a series of graded ethanol solutions (70%, 80%, 90%, 95%, 100% ethanol in dionized water). The dehydrated tissue is then placed in a chamber within a CPD apparatus [block 34] and flushed with liquid $CO_2$ several times to remove the $CO_2$ miscible solvent [block 36]. Drying the tissue using CPD comprises filling the chamber with $CO_2$ [block 40], raising the temperature and pressure to the critical point (for $CO_2$ is 31.1° C. and 1100 psi) [block 42], and then raising the temperature and/or pressure above the critical point [block 44]. For $CO_2$, raising the temperature and/or pressure above the critical point may comprise raising the temperature to between about 42 and about 50° C. and/or raising the pressure to between about 1300 and about 1600 psi. After such treatment, the $CO_2$ is released [block 46]. In some embodiments, release of the $CO_2$ is done slowly, for example at a rate of approximately 100 psi/minute. The release rate of $CO_2$ after treatment may be selected to ensure drying and protecting the microstructures. For example, releasing the $CO_2$ too fast may damage the surface structure of a tissue material. While this embodiment specifically refers to critical point $CO_2$ drying, it is to be appreciated that it may be used with other critical point fluids that may be achieved at temperatures and pressures suitable for biologic tissues.

Figure 3A:
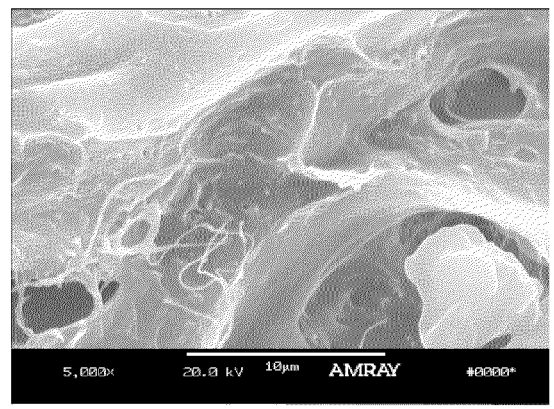
FIG. 3a illustrates a SEM micrograph of demineralized bone fibers dried using lyophilization.
Figure 3B:
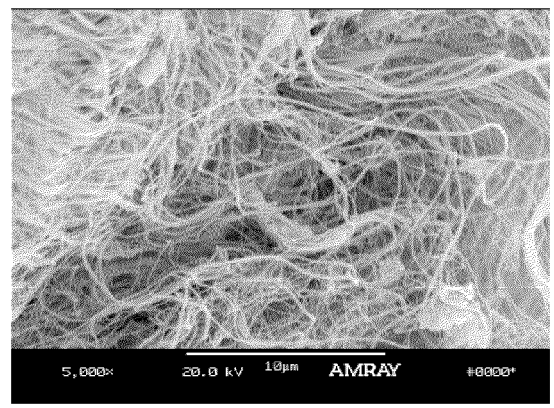
FIG. 3b illustrates a SEM micrograph of demineralized bone fibers dried using supercritical carbon dioxide treatment.
Figure 4:
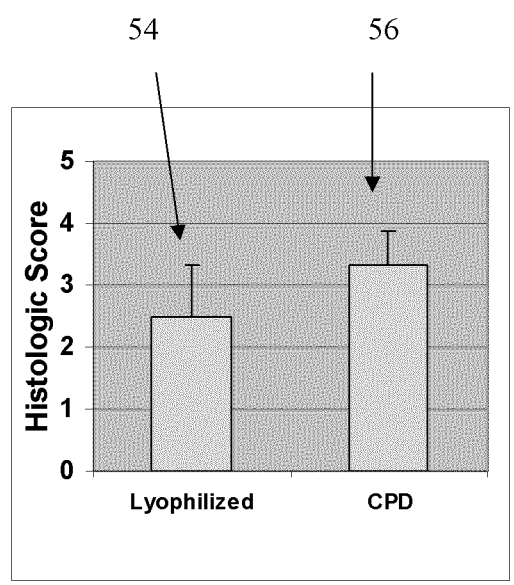
FIG. 4 illustrates a histological score of demineralized bone fibers with and without supercritical carbon dioxide treatment.

Critical point drying substantially protects the delicate surface morphologies of the tissue. FIGS. 3*a* and 3*b* compare the surface morphologies of demineralized bone matrix dried via regular lyophilization 50 (without supercritical $CO_2$ treatment), shown in FIG. 3*a*, and demineralized bone matrix dried via CPD 52 (with supercritical $CO_2$ treatment), shown in FIG. 3*b*. CPD dried DBM 52 shows nanofibrous structures on the surface while lyophilization destroys such structures, as shown by the lyophilized DBM 50. FIG. 4 illustrates the histological scores of demineralized bone fibers dried with lyophilization (without supercritical $CO_2$ treatment) and demineralized bone fibers dried with CPD (with supercritical $CO_2$ treatment), 54 and 56 respectively. As shown, the CPD treated DBM sample, histologic score shown at 56, has higher osteoinductivity than the lyophilized DBM sample, histologic score shown at 54. Without being bound to any theory, it is opined that this may due to the higher surface area of the CPD DBM and/or the nanofibrous structures on the surface. As shown in FIGS. 3, 3*b*, and 4, drying using CPD with supercritical $CO_2$ treatment substantially preserves the natural bone structures and the biological activity.

Drying using CDP with supercritical fluids may be applied to any suitable tissue, as previously discussed. Further, such drying may be applied to more than one type of tissue substantially simultaneously, for example, bone and tendon Further, in some embodiments, such drying may be to tissue and non-tissue material substantially simultaneously. For example, tissue materials may be placed into a polymer mesh covering and then treated with CPD. Under controlled pressure, temperature, treating time, and CO2 release rate, the polymer structures are not affected.

Vi. Viral Inactivation Using Supercritical Fluids

Another embodiment is a method for treating tissues to remove infectious agents and disease-causing pathogens without substantially altering the natural structures of the tissue. In some embodiments, critical and/or supercritical fluids may be used to treat tissues. The tissue retains the desirable macro/micro/nano structures and show high bone formation activity both at heterotopic and orthotopic sites. In another embodiment, a tissue material and a carrier material are treated with supercritical fluid simultaneously. Tissue materials are viral inactivated and terminally sterilized during the incorporation into the carrier material. Thus, tissue grafting material with desirable mechanical properties and tissue regeneration capacity is obtained. For any tissue, the process can be carried out to give viral inactivation and terminal sterilization (if the product is packaged in a porous package with pores small enough to form a bacterial barrier).

In some other embodiments, critical or supercritical fluids are used to remove and/or inactivate viruses and other pathogens from tissue. It acts as a pathogen inactivation and/or sterilization process. Supercritical processing to provide a heat treatment for viral inactivation and killing pathogens retains proteins in a substantially stable position. The proteins contribute to the tissue structure and functioning and are more stable to heat when they are dry (substantially free from water) and free from oxygen. Heating dried tissue in a supercritical $CO_2$ process substantially excludes oxygen, and critical point drying as a preliminary step helps to preserve delicate tissue structures as the water is removed (these structures are then preserved during the supercritical process at higher temperature and pressure). In alternative embodiments, other manners of drying the tissue may be used before supercritical processing for viral inactivation.

Figure 5:
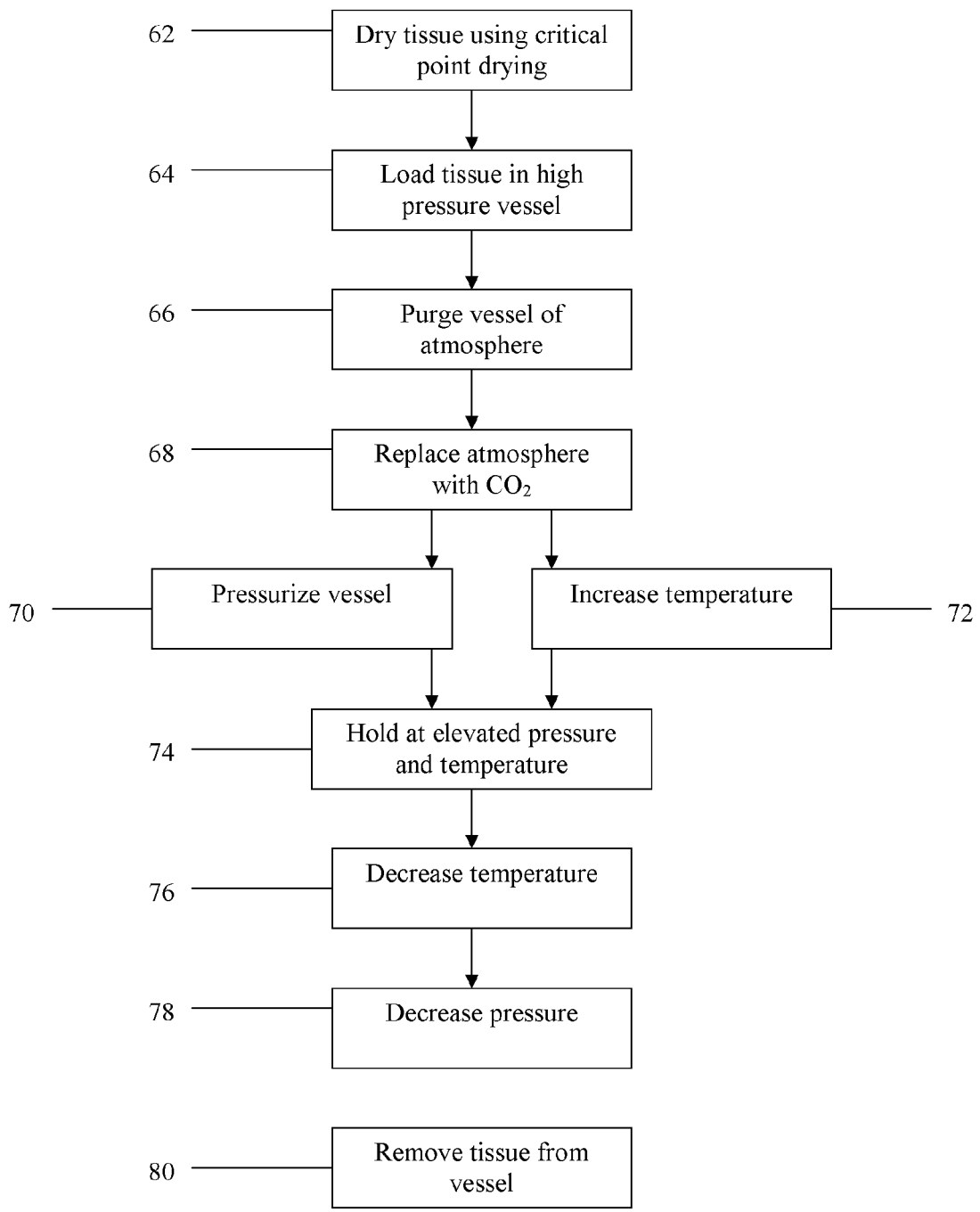
FIG. 5 illustrates a flow chart of critical point drying and tissue inactivation in accordance with one embodiment.

FIG. 5 illustrates a method 60 using critical point drying and further virally inactivating the tissue using a supercritical fluid. As discussed, the kinetics of a pathogen inactivation is an exponential function temperature. Critical point dried tissue may be further treated with a higher temperature and a higher pressure in supercritical fluids to achieve sterilization. Thus, as shown in FIG. 5, the tissue is initially dried using critical point drying [block 62], such as described with respect to FIG. 2. The substantially dry tissue (for example bone or soft tissue) is then loaded in the high pressure vessel [block 64]. In certain embodiments, at the time of loading the temperature of the pressure vessel is between about room temperature and about 80° C. for example 70° C. The loaded pressure vessel is purged of atmosphere [block 66], and the atmosphere being replaced with gaseous $CO_2$ [block 68], for example gaseous $CO_2$ at approximately 700 psi. Purging and replacing may be done simultaneously such that the gaseous $CO_2$ replaces the atmosphere of the vessel in a single step. The vessel is pressurized to an elevated pressure [block 70] while the temperature of the vessel is increased to an elevated temperature [block 72]. In certain embodiments, the temperature of the vessel is increased in a controlled manner, e.g., at a rate of 3.5° C. per minute. The vessel is held at the elevated pressure and elevated temperature for a period of time [block 74], e.g. one hour or less, or about 25 minutes. The vessel may be held, for example, at between about 2500 and about 10,000 psi, between about 5000 psi and about 8000 psi, or at other suitable pressure, and between about 31.1° C. and about 200° C., for example about 105° C., or at other suitable temperature. The vessel temperature is decreased [block 76], actively or passively, below 100° C., for example, to about 90° C., following which the pressure is released [block 78]. Release of the pressure [block 78] may be done slowly, for example, from about 6000 psi to atmospheric pressure in about 10-30 minutes e.g., 20 minutes. The tissue can then be removed from the pressure vessel [block 80].

Figure 6A:
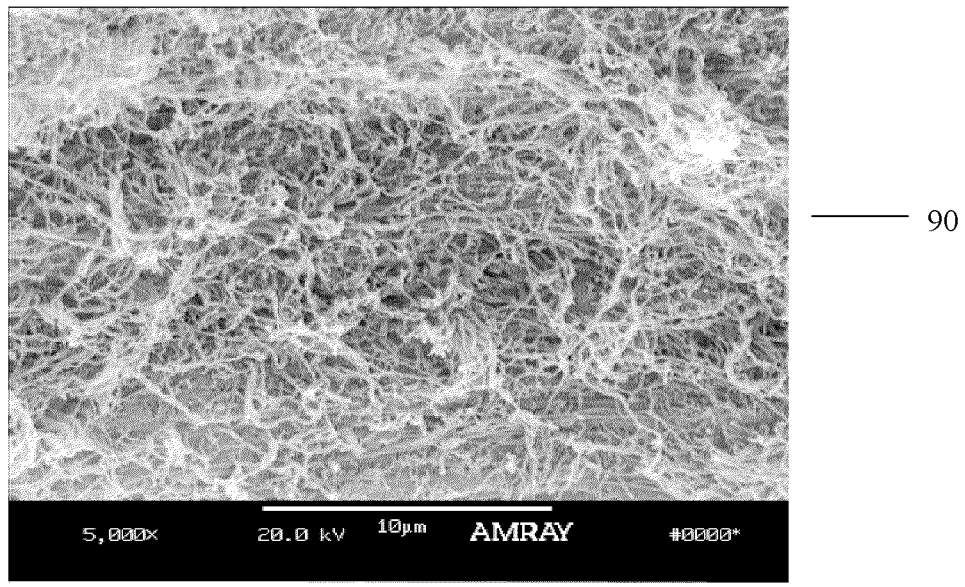
FIG. 6a illustrates a histological score of partially demineralized bone particles treated with supercritical carbon dioxide at 44° C., 1400 psi in accordance with one embodiment.
Figure 6B:
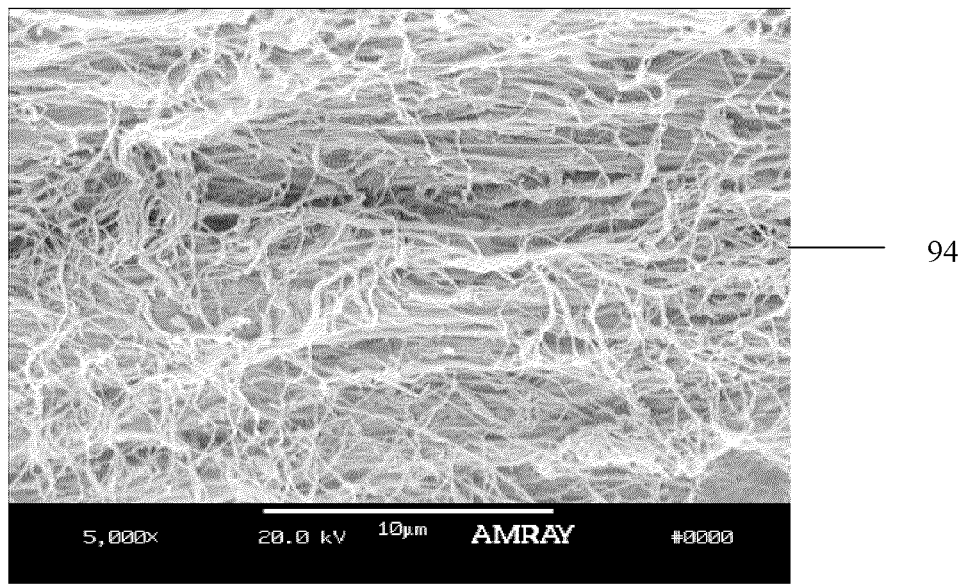
FIG. 6b illustrates a histological score of partially demineralized bone particles treated with supercritical carbon dioxide at 105° C., 7000 psi in accordance with one embodiment.
Figure 7:
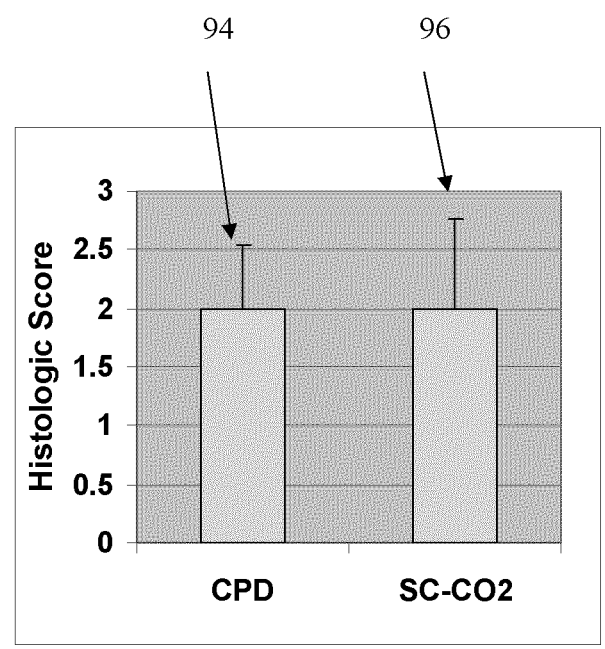
FIG. 7 SEM micrographs of demineralized bone fibers treated with supercritical carbon dioxide at (A) 44° C., 1400 psi and (B) 105° C., 7000 psi in accordance with one embodiment.

High temperature and pressure supercritical $CO_2$ (SC—$CO_2$) treatment (approximately 105° C. and approximately 7000 psi) increases the efficacy of pathogen inactivation. The biological activity of such treated tissues is examined in vivo, the results of which are shown in FIGS. 5*a*, 5*b*, and 6. FIG. 5*a* shows the osteoinductivity of DBM material with CPD treatment 90 (44° C., 1400 psi). FIG. 5*b* shows the osteoinductivity of DBM material with SC—$CO_2$ treatment 92 (105° C., 7000 psi). As shown, there is no significant decrease of osteoinductivity for SC—$CO_2$ treatment of bone material 92. Similarly, the SC—$CO_2$ treatment does not substantially damage the microstructures of DBM. FIG. 6 illustrates histologic scores of DBM material with CPD treatment (44° C., 1400 psi) and DBM material with SC—$CO_2$ treatment (105° C., 7000 psi), 94 and 96, respectively.

In certain embodiments, supercritical treatment for viral inactivation may be applied to issues dried by other methods other than CPD, e.g. lyophilization, vacuum drying, solvent evaporation etc. Further, in some embodiments, critical point drying (CPD, 50° C., 1500 psi) may be combined with supercritical treatment for viral inactivation (SC—$CO_2$, 105° C., 7000 psi) in a one-step process for tissue grafting materials.

Vi. Demineralizing The Bone

In embodiments wherein the tissue is bone, the bone may be at least partially demineralized. More specifically, bone treated to degrade the collagen in the bone, such as by thermal treatment, bone dried using critical point drying, or bone sterilized using critical point fluids, may be demineralized, fully or partially, before or after treatment. Any method of demineralization may be used. In a demineralization procedure in accordance with one embodiment, the bone is subjected to an acid demineralization step. The bone is immersed in acid over time to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment. The demineralized bone is rinsed with sterile water and/or buffered solution(s) to remove residual amounts of acid and thereby raise the pH.

Demineralization is well known in the art and may be performed in any suitable manner. The DBM may be ground or otherwise processed into particles of an appropriate size before or after demineralization. Any of a variety of DBM preparations may be used with the method disclosed herein. DBM prepared by any method may be employed, including particulate or fiber-based preparations, mixtures of fiber and particulate preparations, fully or partially demineralized preparations, mixtures of fully and partially demineralized preparations, surface demineralized preparations, and combinations of these. See U.S. Pat. No. 6,326,018, Reddi et al., Proc. Natl. Acad. Sci. USA (1972) 69:1601-1605; Lewandrowski et al., Clin. Ortho. Rel. Res., (1995) 317:254-262; Lewandrowski et al., J. Biomed. Mater. Res. (1996) 31:365-372; Lewandrowski et al. Calcified Tiss. Int., (1997) 61:294-297; Lewandrowski et al., I Ortho. Res. (1997) 15:748-756, each of which is incorporated herein by reference. Suitable demineralized bone matrix compositions are described in U.S. Pat. No. 5,507,813, hereby incorporated by reference. In some instances, large fragments or even whole bone may be demineralized, and then particulated following demineralization. In other instances, the bone may be particulated prior to demineralization.

Optionally, after demineralization, the bone may be neutralized. Such neutralization may comprise treating the DBM with phosphate-buffered saline (PBS). For example, in one embodiment, 1 g of DBM is placed in 30 ml of PBS (pH7.5) and agitated for approximately 30 minutes.

In some embodiments, a buffer may contain the collagenase. The buffer may be such that it drops the pH of the bone. PBS may then be used to bring the pH of the bone to neutral levels. In other embodiments, the volume of the buffer may be increased to neutralize the pH of the bone.

Vi. Optional Additives

Optionally, other additives may be combined with the treated tissue. Treated tissue is meant to encompass embodiments comprising, for example, a molded tissue and polymer implant. It will be appreciated that the amount of additive used will vary depending upon the type of additive, the specific activity of the particular additive preparation employed, and the intended use of the tissue. The desired amount is readily determinable by the user. Any of a variety of medically and/or surgically useful optional substances can be incorporated in, or associated with, the tissue, before, during, or after treatment.

In certain embodiments, the additive is adsorbed to or otherwise associated with the tissue. The additive may be associated with the tissue through specific or non-specific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the tissue using a linker so that the additive is free to associate with its receptor or site of action in vivo. In other embodiments the additive is either covalently or non-covalently attached to the tissue. In certain embodiments, the additive may be attached to a chemical compound such as a peptide that is recognized by the tissue. In another embodiment, the additive is attached to an antibody, or fragment thereof, that recognizes an epitope found within the tissue. An additive may be provided within the tissue in a sustained release format. For example, the additive may be encapsulated within biodegradable nanospheres, microspheres, etc.

It will be understood by those skilled in the art that the lists of optional substances herewith included are not intended to be exhaustive and that other materials may be admixed with tissue treated as discussed herein.

Angiogenesis Promoting Materials

Development of a vasculature around the implant site may also contribute to forming new bone and/or cartilage tissues. Angiogenesis may be a contributing factor for the replacement of new bone and cartilage tissues. In certain embodiments, angiogenesis is promoted so that blood vessels are formed at the site to allow efficient transport of oxygen and other nutrients and growth factors to the developing bone or cartilage tissue. Thus, angiogenesis promoting factors may be included in the tissue to increase angiogenesis in that region. For example, class 3 semaphorins, e.g., SEMA3, controls vascular morphogenesis by inhibiting integrin function in the vascular system, Serini et al., *Nature*, (July 2003) 424:391-397, incorporated herein by reference, and may be included in the tissue.

Bioactive Agents

The tissue may provide a system for delivering bioactive agents, such as osteoinductive factors, to a host animal. Thus, the tissue enables an improved healing response to the tissue without the need to administer separately the bioactive agent. A problem with the introduction of the bioactive agent at the site is that it is often diluted and redistributed during the healing process by the circulatory systems (e.g., blood, lymph) of the recipient before complete healing has occurred. A solution to this problem of redistribution is to affix the bioactive components to the tissue. Some preferred bioactive agents that can be delivered using a tissue as provided herein include agents that promote the natural healing process, i.e., resorption, vascularization, angiogenesis, new growth, etc. In one embodiment, the tissue is provided with a stabilizing agent, and is used to deliver a biologically active agent. It is expected that the stabilizing agent will protect the biologically active agent from degradation, and therefore will extend its active life after delivery into the recipient animal. In certain embodiments, the bioactive agent is an osteoinductive agent, and in certain embodiments, the tissue may be used to deliver more than one bioactive agent, preferably more than two, and more preferably sometimes more than three bioactive agents. The bioactive agent may be associated with the tissue. For example, the bioactive agent may be associated with the tissue through electrostatic interactions, hydrogen bonding, pi stacking, hydrophobic interactions, van der Waals interactions, etc. In certain embodiments, the bioactive agent is attached to the tissue through specific interactions such as those between a receptor and its ligand or between an antibody and its antigen. In other embodiments, the bioactive agent is attached to the tissue through non-specific interactions (e.g., hydrophobic interactions).

Medically/surgically useful substances include physiologically or pharmacologically active substances that act locally or systemically in the host. Generally, these substances may include bioactive substances which can be readily incorporated into the tissue and include, e.g., soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances can vary widely with optimum levels being readily determined in a specific case by routine experimentation.

Osteoinducing Agents

Osteoinducing agents may be added to the tissue. These agents may be added in an activated or non-activated form. These agents may be added at anytime during the preparation of the tissue. In some embodiments, the tissue is lyophilized in a solution containing the osteoinducing agent. In certain other embodiments, the osteoinducing agents are adhered onto a hydrated tissue and are not freely soluble. In other instances, the osteoinducing agent is added after addition of a stabilizing agent so that the osteoinducing agent is available immediately upon implantation of the tissue.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, the agent may lead to the decreased resorption of bone, etc. Suitable osteoinducing agents include bone morphogenic proteins (BMPs), transforming growth factor (TGF-0), insulin-like growth factor (IGF-1), parathyroid hormone (PTH), and angiogenic factors such as VEGF. In one embodiment, the inducing agent is genetically engineered to comprise an amino acid sequence which promotes the binding of the inducing agent to the DBM or the carrier. Sebald et al., PCT/EPOO/00637, incorporated herein by reference, describe the production of exemplary engineered growth factors suitable for use with DBM.

Vii. Preparing An Implant

Generally Forming an Implant

An implant may be formed from tissue treated according to the various embodiments provided herein. The implant resulting from the tissue, for example from bone, and, optionally carrier, may be flowable, have a putty or gel-like consistency, may be shaped or molded, may be provided as a slurry, may be deformable, and/or may comprise substantially dry pieces held together in a covering. In bone embodiments, the implant may comprise a monolithic bone or may comprise an aggregate of smaller bone elements. The implant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the implant is shaped or moldable, the implant may retain coherence in fluids.

Accordingly, the tissue, especially when comprising as an aggregate of particles, may be subjected to a configuring step to form an implant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized, which may be shaped as a sheet, and processes for fabricating shaped materials from demineralized bone particles is disclosed in U.S. Pat. Nos. 5,507,813 and 6,436,138, respectively, the contents of which are herein incorporated by reference. Suitable sheets include those sold under the trade name Grafton® DBM Flex, which must be wetted/hydrated prior to use to be useful for implantation. Such sheets have recently been reported as effective in seeding human bone marrow stromal cells (BMSCs), which may be useful in the repair of large bone defects. Kasten et al, "Comparison of Human Bone Marrow Stromal Cells Seeded on Calcium-Deficient Hydroxyapatite, Betatricalcium Phosphate and Demineralized Bone Matrix," *Biomaterials*, 24(15):2593-603, 2003. Also useful are tissue preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, poloxamers, resins, clays, calcium salts, and/or derivatives thereof.

In some embodiments, the tissue may have improved spatial properties, such as material handling and packing properties. The improved remodeling properties can further be enhanced by a carrier. In some embodiments, tissue particles may be forced into close proximity, resulting in better osteoconduction. Some carriers may be especially suited for providing improved material handling and packing properties. These include, for example hydrogels such as chitosan and fast resorbing formulations of L-co-G.

Forming an Implant Using SuperCritical Fluids

Critical or supercritical fluids may be used to remove and/or inactivate pathogens from the tissue, as previously described, and then used to incorporate tissue material into a carrier material. The carrier material can be any naturally-derived or synthetic material that has suitable solubility in supercritical fluids. For example, biodegradable polymers such as poly(lactic acid), poly(lactic-co-glycolic acid), polycaprolactone have good solubility in SC—$CO_2$ and may be used as the carrier material.

In certain embodiments, poly(lactic-co-glycolic acid) (PLGA) particles are mixed with DBM fibers and treated with supercritical $CO_2$ at approximately 105° C. with corresponding pressure of approximately 7000 psi in a pressure vessel. After a certain time, e.g. approximately 30 min, $CO_2$ is rapidly released at a rate of approximately 100 psi per second. The sudden degas from polymer materials generates micro and macropores and incorporate DBM fibers into the polymer to form a porous composite. The composite is viral inactivated and sterile. The DBM-PLGA bone grafting materials is osteoinductive due to the presence of active DBM.

Tissue combined with a polymer mesh is useful for certain grafting applications such as hernia repair. If the polymer mesh is made of a suitable material, the fibers of the mesh can be made porous by the supercritical $CO_2$ process. This can help the tissue integration process of the mesh.

VIII. Examples

Example 1

Bone Particles in a Polymer

Bone/polymer osteoimplants were prepared using rabbit bone and a poly DTE polymer.

Bone Preparation

Rabbit femurs were harvested and stored frozen at −60° F. or below. The femurs were thawed in two separate 30 minute soaks in sterile water. After thawing, the femurs were scraped of tissue and coarse ground in a Tekmar mill. Following grinding, the femurs were soaked in sterile 70% ethanol for approximately 45 minutes to an hour, rinsed with sterile water, packaged in Tyvek bags, and frozen. The frozen bone was lyophilized in a Virtus freeze dryer and sealed in foil pouches until use.

Polymer Preparation

PolyDTE polymer was obtained from Integra LifeSciences Holdings Corporation (Plainsboro N.J.). It was packaged in foil pouches until use.

Polymer/Bone Mixing

Approximately 6.57 grams of cleaned and freeze dried rabbit bone, produced as previously described, was combined with approximately 2.19 grams of the DTE polymer and powdered in a liquid nitrogen cooled freeze mill. The freeze mill was operated at a rate of 10 cycles per second with three cycles of 2 minutes each, with 1 minute of cooling therebetween.

Sample Preparation

Approximately 0.37 grams of the mixed/milled material was put in each of 6 cylindrical cavities in a mold mounted in a Carver press. The material was pressurized to 2000 psi and simultaneously heated to 10° C. (212° F.) for 10 to 15 minutes. The compacted, glassy polymer encapsulated the bone and sealed it from air during the heating process. At the end of the heating process, the mold was cooled to approximately 70° C. (158° F.) before the resulting bone/polymer implants were removed from the mold cavities.

Animal Implantation

Each implant was implanted in a drill hole in the femur of a rabbit. After four weeks, three rabbits were sacrificed and the implants examined by histology. There were no signs of inflammation and bone remodeling was occurring. After eight weeks the remaining rabbits were sacrificed. The implants showed almost complete remodeling of the bone.

Example 2

Bone Struts in Hot Supercritical $CO_2$

Six groups of three bovine cortical bone struts were cut from three bovine femurs. Each strut measured 40 mm long with a 4×4 mm cross-section. One strut from each group was kept as a control and lyophilized with no further treatment. One strut from each group was treated in supercritical $CO_2$ at 80° C. (176° F.) for 10 minutes. The remaining strut from each group was treated in supercritical $CO_2$ at 120° C. (249° F.) for 10 minutes. Prior to heating the bone, the chamber was purged with $CO_2$ gas to remove all air. At the end of the heating cycle, the $CO_2$ was released slowly to prevent bone damage as the supercritical $CO_2$ decompressed and escaped from the bone. After treatment, the control and treated struts were lyophilized and sealed in air tight foil pouches until mechanical testing was carried out.

Prior to mechanical testing, the samples were opened from their respective foil-foil pouches and placed in individual 20 ml plastic tube with sufficient saline to completely immerse the struts. The saline comprised 0.9% NaCl at a pH of 5.5. The tubes were capped and left in laboratory ambient conditions for a minimum of twenty-one hours. This rehydration step simulated the condition bone would be in after implantation as a graft.

Calipers were employed to measure the width, height, and length of each strut. The width and height measurements were performed at the mid-span of the strut. The mechanical testing of the struts in three point bending used custom fixtures (sized for the struts) in an MTS minibionix testing machine. Machine settings used were 5N preload and 5 mm/min rate. The raw data was imported into Microsoft Excel where each sample's maximum stress was calculated from the caliper measurements and load at yield from the mechanical testing.

The results showed a 30% drop in strength at both the 80 and 120 degree treatments.

Example 3

Bone Preparation

Rabbit legs were thawed in antiobiotic solution (4 liters DI water+50,000 units of Polymixin B and 50,000 units of Bacitracin) for 1 hour. While in the solution, all soft tissue was scraped from the bones. The proximal and distal ends of the femoral shafts were cut off with a band saw, and the marrow was rinsed from the shafts using tap water. The shafts were soaked in sterile water followed by 1 hour sonication in 70% ethanol.

After clamping in a vise, the shafts were milled to fibers using a straight fluted milling bit with an engagement depth of 0.015 inches and an engagement length of 4 to 5 mm. After collection, the fibers were rinsed with sterile water and sonicated for 30 minutes in 70% ethanol, followed by collection on a 100 micron sieve, and a sterile water rinse. The fibers were defatted by two 30 minute treatments in an ultrasonic ethanol bath.

The fibers were prepared for freeze drying by spreading a thin layer of fibers on a stainless steel tray and double packing in sterile Tyvek, followed by freezing for 30 minutes at $-70°$ C. ($-94°$ F.). Freeze drying was carried out in a Virtus lyophilizer for 18 hours (6 hours at $-35°$ C. ($-31°$ F.) and 12 hours at $35°$ C. ($95°$ F.)) at 500 millitorr pressure. The lyophilized fibers were sieved to a size between 300 and 800 microns (the sieving selected fibers by diameter, not length).

Polymer Preparation

Poly(lactide-co-glycolide) Resomer 84 obtained from Boehringer Ingleheim, was ground in a cryogenic grinder under liquid nitrogen using nine 2 minute cycles run at 10 Hz. There was a 1 minute cool down between each grinding cycle.

Poly(ethylene glycol) was hand ground and sieved to between 212 and 500 microns.

After grinding, the polymers were sealed in double Tyvek pouches and oven dried for 30 minutes; $80°$ C. ($176°$ F.) for the Poly (lactide-co-glycolide) and $40°$ C. ($104°$ F.) for the Poly(ethylene glycol).

Mixing

The polymers and bone were combined in the proportions of: 63% bone, 32% Poly(lactide-co-glycolide), and 5% Poly (ethylene glycol). Mixing was performed in a Turbula mixer for 5 minutes.

Implant Formation

The bone/polymer mixture was pressed into 3.5 mm tablets. Each tablet was loaded individually into a 4.8 mm stainless steel cylinder, and the cylinder, in turn, was placed in a cc pressure chamber in a Supercritical Fluid Technologies (Newark, Del.) Model SG100 supercritical $CO_2$ machine. The machine was set to reach 5000 psi at $105°$ C. ($221°$ F.) and hold this setting for 20 minutes. The temperature was then lowered to $90°$ C. ($194°$ F.) and the $CO_2$ was rapidly released to cause the implant to expand and develop pores.

Finished samples were vacuum packed in pouches until needed.

Animal Surgery

Each implant was implanted in a 5 mm hole drilled in the distal femur of a rabbit. After four weeks, three rabbits were sacrificed and the implants examined by histology. There were no signs of inflammation, and bone remodeling was in progress. After eight weeks, the remaining rabbits were sacrificed. The implants showed almost complete remodeling of the bone.

Example 4

Bone Strips

Human cortical bone was med cleaned and cut into 2-5 mm bone strips. Bone strips were dehydrated using 70%, 93%, and 100% ethanol solutions, each for 30 minutes with shaking. Strips in 100% ethanol were placed into a sterile tyvek pouch. Critical point drying was carried out in a critical point drier (SPI 132000J-AB) using bone dry carbon dioxide as drying media. The critical point for $CO_2$ is $31.1°$ C. with corresponding pressure of 1100 psi. The finishing point is 42-46° C. with corresponding pressure of 1300-1500 psi. After that, $CO_2$ was released slowly in a rate of 100 psi/min. Lipids and cellular debris were removed from the strips.

Example 5

Partially Demineralized Bone Particles

Bone Preparation

Human cortical bone was med cleaned and ground to particles with size between 2.8-4.0 mm using a Fitz mill. The particles were placed into sterile 0.6N HCl for 1.0 hour and washed with sterile deionized water three times.

Critical Point Drying

Partially demineralized bone particles were dehydrated using 70%, 93%, and 100% ethanol solutions, each for 30 minutes with shaking. Particles in 100% ethanol were placed into a sterile tyvek pouch. Critical point drying was carried out in a critical point drier (SPI 132000J-AB) using bone dry carbon dioxide as drying media. The critical point for $CO_2$ is $31._2°$ C. with corresponding pressure of 1100 psi. The finishing point is 42-46° C. with corresponding pressure of 1300-1500 psi. After that, $CO_2$ was released slowly in a rate of 100 psi/min.

Supercritical $CO_2$ Treatment

Bone particles were further treated with $CO_2$ in a Supercritical Fluid Technologies (Newark, Del.) Model SG100 supercritical $CO_2$ machine. Particles in tyvek pouch were placed in the pressure vessel whose temperature was set at $70°$ C. Bone dry $CO_2$ was introduced by an air pump to reach 5000 psi. After that, the vessel was heated up to $105°$ C. and holds this setting for 25 minutes. The temperature was then lowered to $90°$ C. and the $CO_2$ was released.

Bone Repair Testing

Such supercritical $CO_2$ treated partially demineralized bone particles were implanted into a drilled hole in the distal femur of a sheep. The size of defect was 10 mm in diameter and 18 mm in depth. After 13 weeks, the sheep were sacrificed and the explants were examined with MicroCT and histology. The results show significant amount of new bone formed in the defect and the bone particles were almost completely remolded and integrated into host bone.

Osteoinductivity Testing

Such supercritical $CO_2$ treated partially demineralized bone particles were further grounded into small particles with size of 106-500 μm in a Fitz mill and completely demineralized in 0.6N HCl. After washing with water three times, demineralized bone particles (DBM) were lyophilized in a Virtus lyophilizer. Forty milligrams of DBM particles were implanted in athymic rats and the resulting nodules were explanted after 28 days. The explanted nodule was examined histologically and was assigned a numerical score based on a 5-point semiquantitative scale based on percent of nodule area involved in new bone formation. The osteoinductivity score of supercritical $CO_2$ treated DBM particles was the same as DBM particles without supercritical $CO_2$ treatment.

Example 6

Demineralized Bone Fibers

Bone Preparation

Human bone was cut using band saw into strips with 2-5 mm in thickness. The bone strips were put in 0.6N HCl solution and demineralized. After washing demineralized bone strips with deionized water three times, the strips were pressed into fibers using a carver press under the pressure of 4000-5000 psi. Demineralized bone fibers were collected on a 106 micron sieve.

Critical Point Drying

Demineralized bone fibers were dehydrated using 70%, 93%, and 100% ethanol solutions, each for 30 minutes with shaking. Fibers in 100% ethanol were placed into a sterile tyvek pouch. Critical point drying of fibers was carried out in a critical point drier (SPI 13,000J-AB) using bone dry carbon dioxide as drying media. The critical point for $CO_2$ is 31.1° C. with corresponding pressure of 1100 psi. The finishing point is 42-46° C. with corresponding pressure of 1300-1500 psi. After that, $CO_2$ was released slowly in a rate of 100 psi/min.

Supercritical $CO_2$ Treatment

Dried demineralized bone fibers were further treated with $CO_2$ in a Supercritical Fluid Technologies (Newark, Del.) Model SG100 supercritical $CO_2$ machine. Fibers in tyvek pouch were placed in the pressure vessel whose temperature was set at 70° C. Bone dry $CO_2$ was introduced by an air pump to reach 5000 psi. After that, the vessel was heated up to 105° C. and holds this setting for 25 minutes. The temperature was then lowered to 90° C. and the $CO_2$ was released.

Morphology Characterization

The morphologies of demineralized bone fibers were examined with a scanning electron microscope (SEM) (Amray) at ₂0 kV. Demineralized bone fibers with or without supercritical $CO_2$ treatment were mounted on a stub and coated with silver using a sputter coater (Balzer SCD 004). The gas pressure is set at lower than 50 mtorr and the current is about 30 mA. The coating time is 120 seconds. Supercritical $CO_2$ treatment on demineralized bone fibers preserves the natural nanofibrous structures of collagen in bone.

Osteoinductivity Testing

The osteoinductive potential of such treated demineralized bone fibers were tested using a heterotopic osteoinductive 28-day implant model (Edwards et al., *Clin. Orthop. Rel. Res.* 357:219-228, 1998; Urist, *Science* 150:893-899, 1965; each of which is incorporated by reference). Forty milligrams of DBM fibers with or without supercritical $CO_2$ treatment were intramuscularly implanted in athymic rats and the resulting nodules were explanted after 28 days.

The explanted nodule was assessed histologically and was assigned a numerical score based on a 5-point semiquantitative scale based on percent of fiber area involved in new bone formation.

Example 7

Composite of Demineralized Bone Fibers and Polymer

Bone Preparation

Human bone was cut using band saw into strips with 2-5 mm in thickness. The bone strips were put in 0.6N HCl solution and demineralized. After washing demineralized bone strips with deionized water three times, the strips were cut into 5 mm long pieces pressed into fibers using a carver press under the pressure of 4000-5000 psi. Demineralized bone fibers were collected between 106 μm and 2.0 mm sieves.

Critical Point Drying

Demineralized bone fibers were dehydrated using 70%, 93%, and 100% ethanol solutions, each for 30 minutes with shaking. Fibers in 100% ethanol were placed into a sterile tyvek pouch. Critical point drying of fibers was carried out in a critical point drier (SPI 13,000J-AB) using bone dry carbon dioxide as drying media. The critical point for $CO_2$ is 31.1° C. with corresponding pressure of 1100 psi. The finishing point is 42-46° C. with corresponding pressure of 1300-1500 psi. After that, $CO_2$ was released slowly in a rate of 100 psi/min.

Mix with Polymer

DBM fibers are mixed with poly(lactic-co-glycolic acid) (Resomer 824) particles (212-500 μm) in a Turbula mixer for 5 minutes. The mixture is loaded into a stainless steel cylinder which is then placed in a pressure chamber in a Supercritical Fluid Technologies (Newark, Del.) Model SG100 supercritical $CO_2$ machine. Bone dry $CO_2$ is introduced by an air pump to reach 5000 psi. After that, the vessel was heated up to 105° C. and holds this setting for 25 minutes. The temperature is then lowered to 90° C. and the $CO_2$ is released rapidly in 1-2 minutes.

Although the method has been described with reference to preferred embodiments, persons skilled in the art will recognize that changes may be made in form and detail without departing from the spirit and scope of the teachings herein.

What is claimed is:

1. A method of treating tissue comprising the steps of:
   (a) providing tissue comprising cortical bone;
   (b) drying the tissue by a method comprising critical point drying under pressure; and
   (c) sterilizing the tissue by heating the tissue in an inert atmosphere comprising nitrogen in the absence of oxygen,
   wherein step (b) occurs prior to step (c) and the tissue maintains at least approximately 30% of its original strength.

2. The method of claim 1, wherein the tissue further comprises cancellous bone.

3. The method of claim 1, wherein heating the tissue disrupts collagen structure of the tissue.

4. The method of claim 1, further comprising treating the tissue with collagenase.

5. The method of claim 1, further comprising mechanically treating the tissue.

6. The method of claim 1, further comprising chemically treating the tissue.

7. The method of claim 6, wherein chemically treating the tissue comprises treating the tissue with an enzyme.

8. The method of claim 6, wherein chemically treating the tissue comprises treating the tissue with a base.

9. The method of claim 1, further comprising treating the tissue with energy.

10. The method of claim 1, wherein the tissue is bone and further comprising at least partially demineralizing the bone after heating the tissue.

11. The method of claim 1, further comprising drying the tissue after heating the tissue.

12. The method of claim 1, further comprising defatting the tissue before heating the tissue.

13. The method of claim 1, wherein critical point drying comprises:
   providing tissue;
   dehydrating the tissue with a $CO_2$ miscible solvent;
   placing the tissue in a chamber;
   filling the chamber with $CO_2$;
   raising a temperature and the pressure of the chamber to approximately 31.1° C. and approximately 1100 psi; raising the temperature above approximately 31.1° C. and approximately 1100 psi; and releasing the $CO_2$.

14. The method of claim 1, wherein heating the tissue comprises gentle heating of the tissue.

15. The method of claim 14, wherein gentle heating of the tissue denatures proteins within the tissue.

16. The method of claim 1, wherein heating the tissue comprises heating the tissue at approximately 100° C.

17. The method of claim 1, further comprising adding a bioactive agent to the tissue.

18. The method of claim 1, further comprising forming an implant from the tissue.

19. The method of claim 18, wherein forming an implant comprises particulating the tissue, mixing the tissue with a polymer, and treating particulated tissue and polymer mixture with supercritical $CO_2$.

20. The method of claim 19, wherein treating the particulated tissue and polymer mixture with supercritical $CO_2$ is done at approximately 105° C. and approximately 7,000psi.

* * * * *